US012638395B2

(12) United States Patent
Roy et al.

(10) Patent No.: US 12,638,395 B2
(45) Date of Patent: May 26, 2026

(54) SYSTEM AND METHODS FOR PROTEIN DETECTION IN BIOFLUIDS

(71) Applicant: ArcanaBio ehf, Reykjavik (IS)

(72) Inventors: Prithu Roy, Leuven (BE); Daniel Oskarsson, Reykjavik (IS); Dominic Suciu, Edmonds, WA (US); Kristjan Mar Gunnarsson, Hveragerdi (IS)

(73) Assignee: ARCANABIO EHF, Reykjavik (IS)

( * ) Notice: Subject to any disclaimer, the term of this patent is extended or adjusted under 35 U.S.C. 154(b) by 0 days.

(21) Appl. No.: 19/214,623

(22) Filed: May 21, 2025

(65) Prior Publication Data

US 2025/0369884 A1      Dec. 4, 2025

Related U.S. Application Data

(60) Provisional application No. 63/650,105, filed on May 21, 2024.

(51) Int. Cl.
*G01N 21/64* (2006.01)
*G01N 33/68* (2006.01)

(52) U.S. Cl.
CPC ..... *G01N 21/6428* (2013.01); *G01N 21/6408* (2013.01); *G01N 33/6803* (2013.01); *G01N 2021/6419* (2013.01); *G01N 2021/6439* (2013.01)

(58) Field of Classification Search
CPC .............. G01N 21/64; G01N 21/6428; G01N 21/6408; G01N 33/6803; G01N 2021/6419; G01N 2021/6439; G01J 3/44
See application file for complete search history.

(56) References Cited

U.S. PATENT DOCUMENTS

| | | | |
|---|---|---|---|
| 2005/0237522 A1 | 10/2005 | Swift et al. | |
| 2010/0035335 A1 | 2/2010 | Lakowicz et al. | |
| 2011/0053794 A1* | 3/2011 | Zhang .................. | G01N 21/658 |
| | | | 506/22 |
| 2012/0097864 A1* | 4/2012 | Takahashi .......... | G01N 21/6452 |
| | | | 250/208.1 |
| 2013/0073221 A1* | 3/2013 | Attinger ................ | G16C 20/20 |
| | | | 702/30 |
| 2018/0166267 A1* | 6/2018 | Pyun ...................... | H01J 49/049 |
| 2020/0064323 A1* | 2/2020 | Doshi .................. | G01N 27/128 |
| 2020/0072668 A1* | 3/2020 | Han ........................ | G01J 3/027 |
| 2022/0319207 A1* | 10/2022 | Yamane ............. | G01N 21/6458 |
| 2022/0365075 A1 | 11/2022 | Knowles et al. | |

OTHER PUBLICATIONS

Sarkisyan et al., Local fitness landscape of the green fluorescent protein. (2016) *Nature *. DOI: 10.1038/nature 17995.

(Continued)

*Primary Examiner* — Abdullahi Nur

(74) *Attorney, Agent, or Firm* — Richard T. Black; FISHERBROYLES LLP

(57) ABSTRACT

An apparatus and method for identifying a protein or proteins in a sample of a biofluid. The identification is based on illuminating the sample with ultraviolet radiation and detecting and analyzing the resulting fluorescence. A trained model may be used to determine a protein responsible for a spectra detected from the illumination of the sample.

30 Claims, 14 Drawing Sheets

(56) References Cited

OTHER PUBLICATIONS

Roy et al., Preventing Corrosion of Aluminum Metal with Nanometer-Thick Films of Al2O3 Capped with TiO2 for Ultraviolet Plasmonics; ACS Appl. Nano Mater. Jun. 19, 2021, 4, 7, 7199-7205, @ 2021 American Chemical Society, United States.

Barulin et al., Deep UV plasmonic enhancement of single protein autofluorescence in zero-mode waveguides. Nano Lett. 2019, 19, 10, 7434-7442, Sep. 17, 2019, https://pubs.acs.org/doi/10.1021/acs.nanolett.9b03137; @ 2019 American Chemical Society; Aix Marseille Univ, CNRS, Central Marseille, Institut Fresnel, 13013 Marseille, France:.

Roy Prithu et al., Ultraviolet Resonant Nanogap Antennas with Rhodium Nanocube Dimers for Enhancing Protein Intrinsic Autofluorescence, ACS Nano (2023), 17, 22418-22429.

Levene et al., Zero-Mode Waveguides for Single-Molecule Analysis at High Concentrations. *Science*. (2003) DOI: 10.1126/science.1079700 (2003).

Lakowicz, J. R., Principles of Fluorescence Spectroscopy. New York: Plenum Press. (1983) ISBN-10: 0-387-31278-1; ISBN-13: 978-0387-31278-1.

Barulin et al., Ultraviolet optical horn antennas for label-free detection of single proteins. *Nature Communications*. (2022) DOI: doi:10.1038/s41467-022-29546-4.

Balasco et al., A Comprehensive Analysis of the Intrinsic Visible Fluorescence Emitted by Peptide/Protein Amyloid-like Assemblies. *International Journal of Molecular Sciences*. (2023) DOI: 10.3390/ijms24098372.

Nantasenamat Chanin et al., Prediction of GFP spectral properties using artificial neural network. *Journal of Computational Chemistry*. (2007) DOI: doi:10.1002/jcc.20656.

Hixon et al., Algorithm for the Analysis of Tryptophan Fluorescence Spectra and Their Correlation with Protein Structural Parameters. *Algorithms*. (2009) DOI: doi:10.3390/a2031155.

Niyangoda et al., Carbonyl-based blue autofluorescence of proteins and amino acids. *PLOS One*. (2017) DOI: doi:10.1371/journal.pone.0176983.

Wang Tao et al., Aggregation-Induced Dual-Phosphorescence from Organic Molecules for Nondoped Light-Emitting Diodes. *Advanced Materials*. (2019) DOI: doi:10.1002/adma.201904273.

Roy et al., Preventing Corrosion of Aluminum Metal with Nanometer-Thick Films of Al2O3 Capped with TiO2 for Ultraviolet Plasmonics, ACS Appl. Nano Mate. Jun. 19, 2021, 4, 7, 7199-7205.

Barulin et al., Deep UV plasmonic enhancement of single protein autofluorescence in zero-mode waveguides. Aix Marseille Univ, CNRS, Central Marseille, Institut Fresnel, 13013 Marseille, France, Nano Lett. 2019, 19, 10, 7434-7442, Sep. 17, 2019.

* cited by examiner

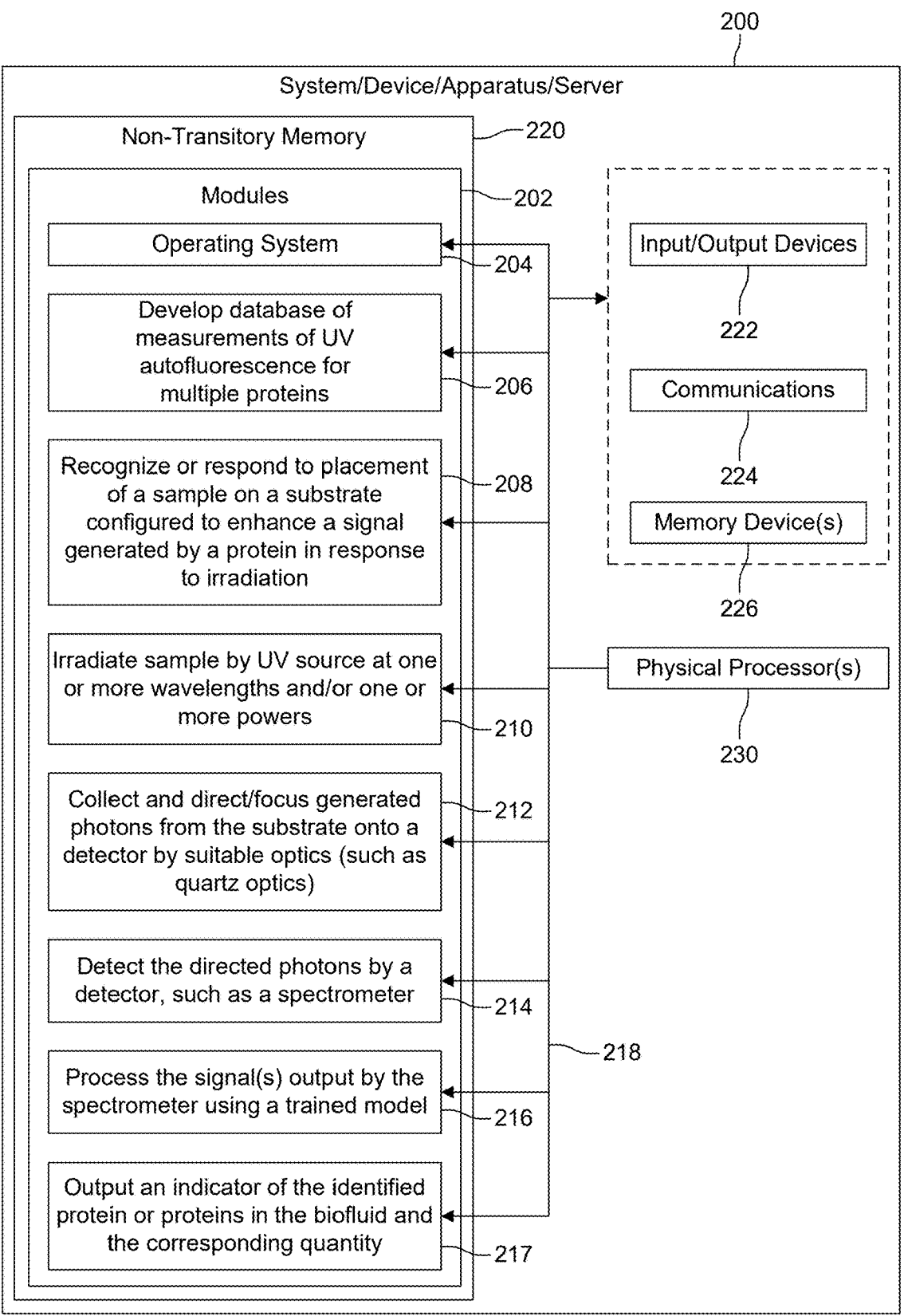

200

System/Device/Apparatus/Server

Non-Transitory Memory ~220

Modules ~202

Operating System ~204

Develop database of measurements of UV autofluorescence for multiple proteins ~206

Recognize or respond to placement of a sample on a substrate configured to enhance a signal generated by a protein in response to irradiation ~208

Irradiate sample by UV source at one or more wavelengths and/or one or more powers ~210

Collect and direct/focus generated photons from the substrate onto a detector by suitable optics (such as quartz optics) ~212

Detect the directed photons by a detector, such as a spectrometer ~214

Process the signal(s) output by the spectrometer using a trained model ~216

Output an indicator of the identified protein or proteins in the biofluid and the corresponding quantity ~217

~218

Input/Output Devices

222

Communications

224

Memory Device(s)

226

Physical Processor(s)

Filter based Detection Scheme

Simple Dichroic

Optical Filters

Lens System for Focusing and Beam Expanding

SYSTEM AND METHODS FOR PROTEIN DETECTION IN BIOFLUIDS

CROSS REFERENCE TO RELATED APPLICATION

This application claims the benefit of U.S. Provisional Application No. 63/650,105, entitled "System and Methods for Protein Detection in Biofluids," filed May 21, 2024, the disclosure of which is incorporated, in its entirety (including the Appendices) by this reference.

BACKGROUND

In biomedical contexts, a biomarker or biological marker, is a measurable indicator of a specific biological state or condition. Biomarkers are often measured and evaluated using saliva, blood, urine, or soft tissues to examine normal biological processes, pathogenic processes, or pharmacologic responses to a therapeutic intervention. As such, the detection and measurement of biomarkers is one of the tools used to assist in diagnosing a disease or condition, or for monitoring a person's response to a medication or treatment.

The need for rapid and accurate detection of protein biomarkers in biofluids is critical in medical diagnostics. However, current technologies and conventional approaches often require extensive pre-processing, are time-consuming, and require specialized equipment.

Proteins are the building blocks of all organisms. Apart from many other roles, many proteins found in human bodily fluids are also biomarkers and can be indicators of health and diseases. Biofluids such as blood, saliva, serum, tears, urine, interstitial fluid or cerebrospinal fluid contain traces of different protein biomarkers. As a result, analyzing their concentration(s) and molecular state is believed key to the development of effective and accurate bio-diagnostic devices and techniques.

There are several conventional techniques used to detect proteins in biofluids, but the most frequently used technique relies on antibodies and the labeling of proteins to differentiate between them. However, the present approach requires excessive time and trained personnel or is specific to a single kind of disease and therefore is not practical for regular or frequent diagnosis of multiple biomarkers.

What is desired are systems, apparatuses, devices, and methods for efficiently and accurately, quickly detecting and measuring one or more protein biomarkers found in biofluids without a requirement of pre-processing or labelling. Embodiments of the disclosure overcome one or more disadvantages of conventional approaches and address this and other objectives both individually and collectively.

SUMMARY

The terms "invention," "the invention," "this invention," "the present invention," "the present disclosure," or "the disclosure" as used herein refer broadly to the subject matter disclosed and/or described in this document, the drawings or figures, and to the claims. Statements containing these terms do not limit the subject matter disclosed or described, or the meaning or scope of the claims. Embodiments of this disclosure are defined by the claims and not by this summary. This summary is an overview of various aspects of the disclosure and introduces some of the concepts that are further described in the Detailed Description section. This summary is not intended to identify key, essential, or required features of the claimed subject matter, nor is it intended to be used in isolation to determine the scope of the claimed subject matter. The subject matter should be understood by reference to appropriate portions of the entire specification, to any or all figures or drawings, and to each claim.

Embodiments are directed to systems, devices, and methods in the field of biomedical diagnostics and more specifically, to an integrated system combining UV spectroscopy techniques, a nanophotonic-microfluidic substrate for sample handling, optical hardware to illuminate and detect a UV signal from a sample, and analytical techniques (such as an advanced model) for the detection, identification, and quantification of proteins in a biological fluid sample. The disclosed system addresses the challenges and disadvantages of conventional approaches by leveraging the intrinsic emission properties of proteins and non-proteogenic amino-acids that emit UV using UV spectroscopy, as enhanced by technically advanced hardware and artificial intelligence-based data processing techniques.

An aspect of disclosed and/or described system and methods is the use of UV autofluorescence of complex molecules such as proteins to create a set of unique spectra or "signatures". These unique signatures are then used to differentiate and detect different proteins in complex biological mixtures such as (for example) within saliva, sweat, urine, tears, blood, interstitial fluid, or cerebrospinal fluid.

In one embodiment, a system collects multiple items of data for a specific single molecule of protein and uses that data (in whole or in part) in a process to identify the proteins in a sample of a biofluid. The collected data may be obtained by use of the disclosed apparatus and processes for a set of known (that is, previously identified) proteins, resulting in a reference dataset containing examples of spectra (or spectrums) and an associated identification of the protein or proteins responsible for generating the spectra. The collected data may be augmented by spectra or spectrum obtained by other investigators. Although reference is made to protein molecules, an embodiment of the disclosed system or methods may also be applied to a single amino acid or molecule other than a protein.

The collected data is used as a reference source to identify a spectra or spectrum obtained from a sample. Identification of the protein or proteins responsible for generating a spectra may be performed by a trained model (such as one trained on the previously collected reference data) or a suitable signal processing, image processing, or comparison technique.

Data acquisition for a set of characterized proteins or experimental samples can be performed by irradiating the proteins under a range of controlled conditions, including one or more of:

Variation of excitation wavelengths;

Adjustment of power levels specific to each excitation wavelength;

Implementation of cycle modulation at varying power levels to mitigate photobleaching effects;

Alteration of the polarization state of the excitation radiation;

Modulation of sample temperature (e.g., for biofluid analysis); and

Analysis of protein distribution across different fractions, categorized by properties such as isoelectric point, molecular size, or affinity.

The collected data represents multiple measurements of the UV autofluorescence emission of a molecule of a protein in a sample for the different inputs. In one embodiment, the system collects multiple spectra ranging from 250 nm to 500 nm in wavelength (as an example), thereby creating multi-dimensional signatures of proteins that may be present in a sample. Although reference is made to protein molecules, as noted the disclosed approach may be applied to other substances. As non-limiting examples, such substances include Serotonin and Melatonin that are derived from Tryptophan, L-DOPA and Dopamine that are derived from Tyrosine, and compounds not derived from the aromatics amino acids such as Neopterin, Porphyrins and Nicotinamide Adenine Dinucleotide.

In one embodiment, the signal or signals obtained from a protein upon irradiation and subsequent emission are enhanced by use of a "smart" substrate on which a sample is positioned. The substrate may consist of one or more nanophotonic structures. As non-limiting examples, these may include a UV dimer antenna, a Nanoaperture, or other suitable nano-photonic structure that functions to enhance signals emitted by a protein, typically by enhancing the quantum yield of emitter(s) inside the protein or other analyte. The amount of output photons can be estimated as the absorption coefficient times quantum yield, where the absorption coefficient measures how much of the excitation energy is captured by a target and quantum yield represents how much of that is emitted as a photon.

In some embodiments, the nanophotonic structures provide two primary benefits:

Optical enhancement of protein autofluorescence (such as an increase in signal-to-noise, and increase in photons generated); and Reducing background noise by providing a sub-diffraction diffraction spot, as with the use of a Zero Mode Waveguide (as a non-limiting example). Sub-diffraction nano-apertures such as zero mode waveguides isolate a sample in a relatively small (e.g., attoliter) detection volume, which results in a very low number of analytes (i.e., single molecule resolution) in a detection volume.

The use of sub-diffraction-limited detection volumes reduces the number of molecules detected at each point to single-molecule or few-molecule resolution for a given analyte within a heterogeneous solution. This reduction enables effective deconvolution of spectral signatures. By performing detection and deconvolution across multiple locations, it becomes possible to reconstruct the concentration profile of the sample under investigation. Deploying an array of sub-diffraction detection volumes allows this process to be performed in parallel. Sufficient data can thus be collected to achieve accurate, efficient, and label-free detection of a wide range of proteins within complex mixtures. The detection process can occur either during the diffusion phase, wherein proteins or other biomolecules move freely in solution, or under conditions where diffusion is arrested or otherwise restricted.

The signal collected is then directed by quartz optics to a spectrometer, in one example implemented in the form of a CMOS image sensor. By using a large array of sub-diffraction detection volumes, each providing an independent measurement with a distinct combination of molecular occupancies, the system generates a rich dataset that captures statistical variations across the sample. These multiple independent fluorescence readings can be mathematically combined and analyzed as a system of equations, allowing deconvolution of the overall sample composition with high accuracy.

Unlike conventional bulk fluorescence measurements, which average all molecules together and obscure minority components, the sub-diffraction array approach preserves discrete molecular information, enabling reconstruction of complex mixtures by solving for the concentrations of individual species through advanced spectral unmixing and statistical modeling. This approach substantially improves both the sensitivity and the resolution of biomarker detection in heterogeneous biological fluids.

The collected signals from the spectrometer or sensor are processed by an algorithm/model which performs spectral unmixing (decomposition of a more complex spectrum) and other forms of signal and data processing. In one embodiment, the model is trained on a high-fidelity dataset created by obtaining spectra of different pure proteins, as well as from artificial mixtures and biological samples.

Embodiments implementing an example of the disclosed and/or described approach are able to achieve detection of different protein biomarkers inside biological mixtures in the absence of labels (i.e., without knowing a priori what the protein responsible for generating a detected spectrum is). The efficiency and effectiveness of the disclosed and/or described approach provides an ability to conduct frequent and almost continuous monitoring of the presence or absence of specific biomarkers in the form of proteins. Among other applications or use cases, the resulting data can be used to monitor or survey multiple health-related conditions and diseases across different locations and times. In addition to the protein biomarkers discussed, there are stand-alone amino acids, and some organic molecules and inorganic molecules that can be irradiated to produce UV emissions and may be advantageous to detect and identify.

The hardware and software components or processes disclosed and/or described may be used to acquire a spectrum or spectra from a sample placed on the substrate. Further, where needed, the components and processes may be used to create or augment a database of spectra for multiple proteins that serves as a reference or guide in determining the protein or proteins detected in a sample.

In some embodiments, the systems, apparatuses, and methods disclosed and/or described herein for a diagnostic system or tool comprise the following:

A process to assemble and prepare a dataset where each item of data is a spectrum or set of spectra for a protein, the dataset serving as a reference for comparison with the spectrum or spectra of a sample;

This may be performed by experimental methods and/or accessing previously obtained spectra for specific proteins and assembling them into a database; and A process to collect and pre-process a sample and control the irradiation and collection of fluorescence from the sample, followed by performing a comparison between the spectrum or spectra of the collected sample and one or more items of data in the dataset.

In one embodiment, the reference dataset and the sample spectra may be obtained through the use of the following process and components:

A process which creates a set of spectra of aromatic and non-aromatic proteins, where when irradiated/excited, the proteins produce/emit a UV fluorescence. The set of spectra are collected at a plurality of combinations of input parameters for the source of excitation (including wavelength, power/intensity, and polarization, as non-limiting examples) to create a unique signature of a protein within a complex biological media;

A nanophotonic-microfluidic substrate upon which a protein being used to construct the reference dataset or a sample is placed. The substrate enhances the detection of signals emitted by the excited proteins. The substrate and micro-fluidic channels may be part of the same or different elements or components. The substrate may include a fluid pump, with control elements generally separate and positioned off the substrate;

A UV source for illuminating a sample (e.g., a biofluid) using a plurality of combinations of source inputs or controls (e.g., wavelength, power, polarization) to excite fluorescence in the sample. A corresponding unit to detect and interpret the emitted radiation from the sample and determine its spectra (e.g., a CMOS spectrometer or other form of detector with an optical bandpass filter); and An algorithm/model that interprets the spectral data obtained from a sample and compares it to one or more spectra contained in the reference dataset to identify and quantify protein biomarkers found in the sample. In some embodiments, the model is a trained Machine Learning model operating as a classifier.

Other objects and advantages of the disclosed systems, apparatuses, and methods will be apparent to one of ordinary skill in the art upon review of the detailed description and the included figures. Throughout the drawings, identical reference characters and descriptions indicate similar, but not necessarily identical, elements. While the embodiments disclosed or described herein are susceptible to various modifications and alternative forms, specific embodiments are shown by way of example in the drawings and are described in further detail herein. However, embodiments are not limited to the specific or example forms described. Rather, the disclosure covers all modifications, equivalents, and alternatives falling within the scope of the appended claims.

BRIEF DESCRIPTION OF THE DRAWINGS

Embodiments of the disclosure are described with reference to the drawings, in which:

FIG. 2 is a diagram illustrating elements or components that may be present in a computing device or system configured to implement a method, process, function, or operation in accordance with some embodiments;

Note that the same numbers are used throughout the disclosure and figures to reference like components and features.

DETAILED DESCRIPTION

One or more embodiments of the disclosed subject matter are described herein with specificity to meet statutory requirements, but this description does not limit the scope of the claims. The claimed subject matter may be embodied in other ways, may include different elements or steps, and may be used in conjunction with other existing or later developed technologies. The description should not be interpreted as implying any required order or arrangement among or between various steps or elements except when the order of individual steps or arrangement of elements is explicitly noted as being required.

Embodiments of the disclosed subject matter are described more fully herein with reference to the accompanying drawings or figures, which illustrate examples by which the disclosed systems, apparatuses, devices, and methods may be practiced. However, the disclosure may be embodied in different forms and should not be construed as limited to the embodiments set forth herein; rather, these embodiments are provided so that this disclosure will satisfy the statutory requirements and convey the scope of the disclosure to those skilled in the art.

In the context of the disclosure, the following terms have at least the indicated meaning:

Nanostructure—nanometer structures such as nano wells, nanoantenna or any other nanophotonic structures;

Nanophotonic—Nanometer size structure that can modify optical properties at photon scale;

Micro-fluidic—fluid handling using micrometer channels in substrates;

Detector—detector to collect photon and give photo statistics as output;

Nano-well—Cylindrical hole in metal film also none as Zero mode waveguide;

Micro-fluidic—"Micro-fluidic" refers to the technology, devices, or systems that process, manipulate, or analyze fluids at the microliter or nanoliter scale, typically within channels or compartments with at least one dimension between 1 µm and 1000 µm. It includes passive or active control of fluid flow, mixing, separation, or reaction, and may be implemented in integrated devices using any material or fabrication method;

Detector—"Detector" refers to any device, system, or mechanism capable of receiving, quantifying, analyzing, or responding to one or more signals, including optical, electrical, thermal, acoustic, or chemical signals. A detector may perform analog or digital signal transduction, and may include components for amplification, filtering, or processing of said signals, whether as discrete or integrated elements;

Biomarker—"Biomarker" refers to any measurable substance, signal, or biological feature whose presence, concentration, structure, or activity provides information about a biological state, process, or condition. This includes, but is not limited to, proteins, peptides, nucleic acids, metabolites, exosomes, small molecules, cellular components, or physicochemical parameters such as pH, salinity, or viscosity.

Figure 1:
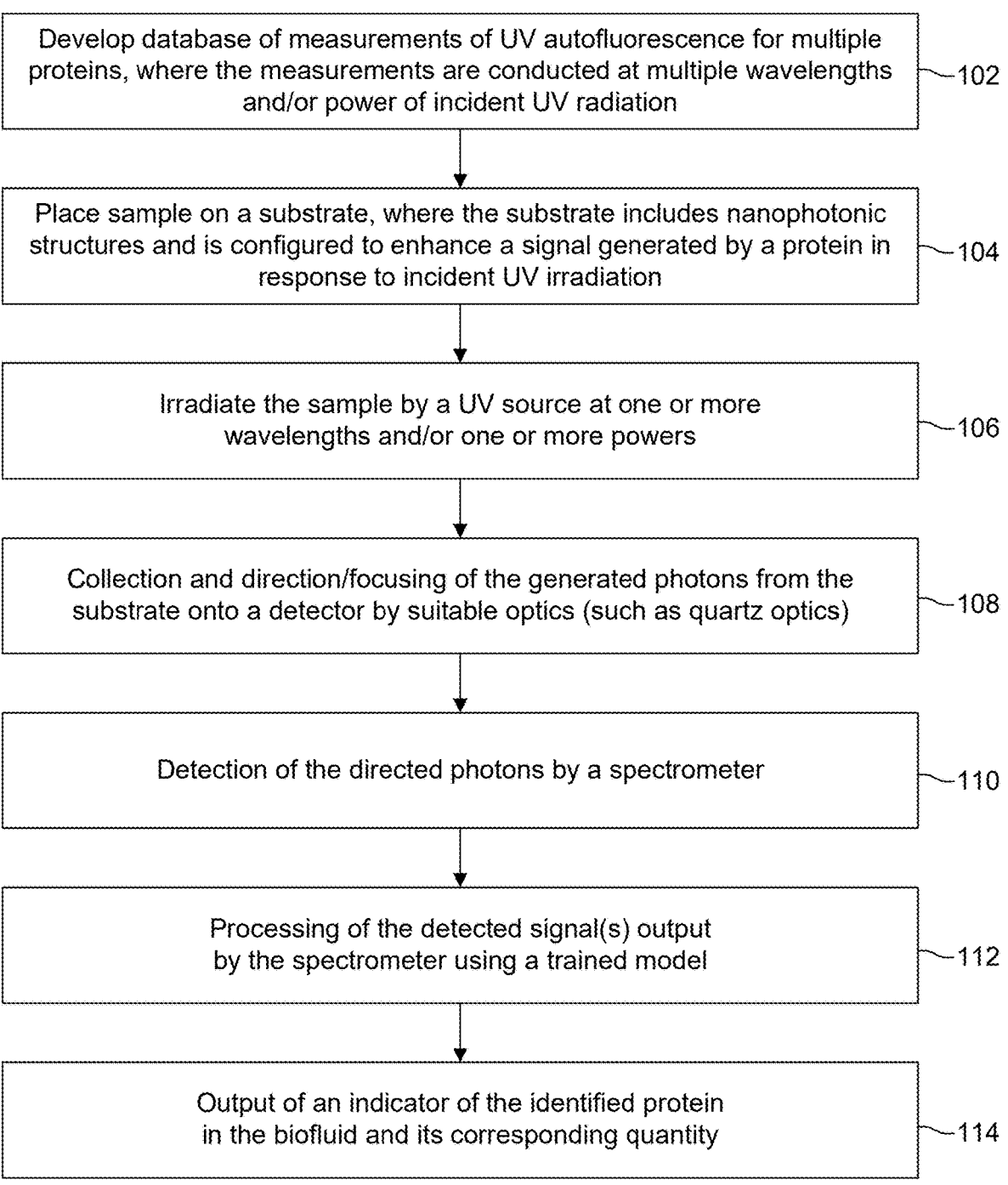
FIG. 1 is a flowchart or flow diagram illustrating a set of steps, stages, processes, operations, or functions that may be used to implement an embodiment of the disclosure.

In one non-limiting example embodiment, a method for detecting, identifying, and quantifying a biomarker in the form of a protein may comprise the following steps, stages, operations, functions, or processes (as illustrated in FIG. 1, which is a flowchart or flow diagram illustrating a set of steps, stages, processes, operations, or functions that may be used to implement an embodiment of the disclosure):

Development of a database of measurements of UV autofluorescence for multiple proteins, where the measurements are conducted at multiple wavelengths and/ or power level of incident UV excitation, as nonlimiting examples (as suggested by step or stage 102);

The database may be used to train a model to act as a classifier that takes an input spectrum or spectra and outputs an indication of a protein responsible for producing that spectrum or spectra;

The database may be assembled from a combination of experimental measurements made using the disclosed system and processes, and previously collected spectra;

Placement of a sample on a substrate, where the substrate is configured to enhance a signal generated by a protein in response to incident UV excitation (as suggested by step or stage 104);

In one embodiment, the substrate comprises one or more nanophotonic structures which serve to enhance or amplify the signal or signals generated by the protein in response to the incident excitation;

In one embodiment, the substrate may be patterned with a plurality of nano-wells, with each such well defining a stochastic volume of small enough size that molecular diffusion results in changes to the occupancy or contents of the nano-well over time;

Here the use of the term "stochastic volume" is meant to convey that each sampling event is subject to statistical fluctuations due to the low number of molecules present in a well;

Note that for purposes of creating the referenced database, the "sample" may be a protein whose identify is known;

Irradiation/Excitation of the sample by a UV source at one or more wavelengths and/or one or more power levels (as suggested by step or stage 106);

In some embodiments, the source of UV excitation may be a laser or LED;

The wavelength of the source may be varied between 180 nm and 300 nm in one example embodiment;

In some embodiments, a filter may be used to selectively produce desired wavelength(s) of output photons for the source;

In some embodiments (and depending upon the reference dataset available and its features), the UV source and other components may be configured such that the incident excitation is at different wavelengths, powers, and polarizations, among other characteristics;

Collection and direction/focusing of the generated photons/emission from the substrate onto a detector by suitable optical elements (e.g., quartz optics, lenses, or holographic elements) (as suggested by step or stage 108);

Detection of the directed photons by a spectrometer (e.g., a fabricated CMOS device) (as suggested by step or stage 110);

Processing of the detected signal(s) output by the spectrometer using a trained model (as suggested by step or stage 112);

In one embodiment, the trained model performs spectral unmixing (decomposition) followed by data processing to prepare the detected signal(s) for identification as being produced by a specific protein or proteins;

Identification of the protein responsible for the generated photons and the signals generated by the spectrometer may be performed by the trained model, which functions as a classifier, and/or by reference to a previously collected set of spectra characterizing different proteins (as described with regards to step or stage 102);

Output of an indicator of the identified protein or proteins in the biofluid and the corresponding quantities (based on the intensity of the generated emission, which corresponds to the number of photons and hence interactions between the protein and the incident UV excitation) (as suggested by step or stage 114).

In one embodiment, a corresponding apparatus or device for the generation and collection of a spectrum or spectra produced by a protein in response to UV irradiation may comprise the following elements, components, structures, or modules:

A substrate on which to place a sample, the substrate including one or more nanophotonic structures that operate to enhance a signal/photons incident on the nanophotonic structures;

In a typical use case, the substrate would operate to enhance or amplify the signal/photons generated by a sample after the sample's exposure to incident UV excitation;

A source of UV excitation positioned to illuminate the sample, and operable to generate the incident radiation at a plurality of wavelengths and a plurality of power levels (as examples, although other characteristics of the incident radiation may be varied);

One or more optical elements to focus the incident UV excitation on the sample/substrate and/or to focus photons emitted by the nanophotonic structures onto a detector;

A detector to receive emitted photons from the illuminated sample (after interaction with the nanophotonic structures) and to respond to one or more wavelengths of the received photons (such as by generating signals corresponding to a spectrum or spectra of the fluorescence of the sample when irradiated); and A programmed processor executing a set of computer-executable instructions that cause the apparatus or device to identify a protein or proteins in the sample based on the identified one or more wavelengths in the received photons, wherein the process or processes performed by execution of the instructions include using a trained model that takes as an input a spectrum of emitted photons and in response outputs a protein or proteins responsible for generating the spectrum;

In one embodiment, the device may communicate to a remote server using a wireless communication capability, where the serve may host a database of spectra used as a reference, and/or a trained model that operates to identify a protein based on its spectrum;

The database and/or model may be updated using data or spectra collected by a device.

Examples of each of the structures, elements, components, or modules that may be used in implementing one or more embodiments of the disclosure are described in greater detail later in this specification with reference to FIGS. 3-13.

The following sections provide further information on the fundamental concepts underlying embodiments of the disclosed and/or described system, apparatus, and methods and in some cases include references to relevant research.

Source and Strength of UV Autofluorescence of Proteins

The ultraviolet (UV) autofluorescence of a protein is a multifaceted phenomenon driven by several molecular sources. The primary contributors are aromatic residues-tryptophan (Trp), tyrosine (Tyr), and phenylalanine (Phe)-which absorb UV light and emit characteristic fluorescence. Additional factors such as protein concentration, aggregation, and the presence of carbonyl double bonds may also impact the observed fluorescence signals.

In complex biological fluids such as saliva or sweat, emissions from aromatic amino acids (300-400 nm) and carbonyl bonds (380-500 nm) combine to create distinct UV spectral fingerprints. Aromatic amino acids are the dominant fluorophores under UV excitation, with tryptophan generally providing the strongest emission due to its higher quantum yield. However, other sources also contribute, such as a deep blue autofluorescence linked to carbonyl bonds, independent of aromatic residues. Moreover, the protein photolumines-
cence intensifies with increasing concentration and aggre-
gation, while protein conformation further modulates UV-
induced visible fluorescence.

To accurately map protein autofluorescence, excitation
across multiple UV wavelengths (typically 200-300 nm) is
employed. Recording the resulting emission spectra captures
a weighted response from all intrinsic fluorophores within
the irradiated protein. This approach allows for the construc-
tion of comprehensive spectral profiles, sensitive to varia-
tions in amino acid composition and structural features.

The uniqueness of a protein's spectrum stems not only
from the number of aromatic residues but also from their
microenvironment within the protein structure. Studies have
shown that tryptophan emission varies based on its local
environment, leading to at least five distinct emission sub-
categories. Selective excitation at the absorbance peaks of
Tyr and Phe further enriches the spectral dataset, enabling a
more nuanced differentiation between proteins based on
subtle structural differences.

Ultimately, a protein's UV autofluorescence signature
results from the integrated contributions of multiple aro-
matic residues, modified by protein folding and aggregation
state. By capturing spectra at multiple excitation wave-
lengths and factoring in structural influences, a unique,
multidimensional spectral map can be generated for each
protein, providing a powerful tool for label-free protein
characterization within complex mixtures.

In another non-limiting embodiment, time-resolved fluo-
rescence measurements are performed to further character-
ize the proteins or analytes of interest. Fluorescence lifetime
and decay profile information is collected in addition to
steady-state spectral features. These time-resolved charac-
teristics provide complementary data regarding the molecu-
lar environment, quenching interactions, and conformational
states of the biomolecules. Such measurements enable
enhanced differentiation between species that may exhibit
overlapping steady-state spectra but distinct temporal emis-
sion behaviors, thereby improving the sensitivity and speci-
ficity of the detection process.

Figure 14:
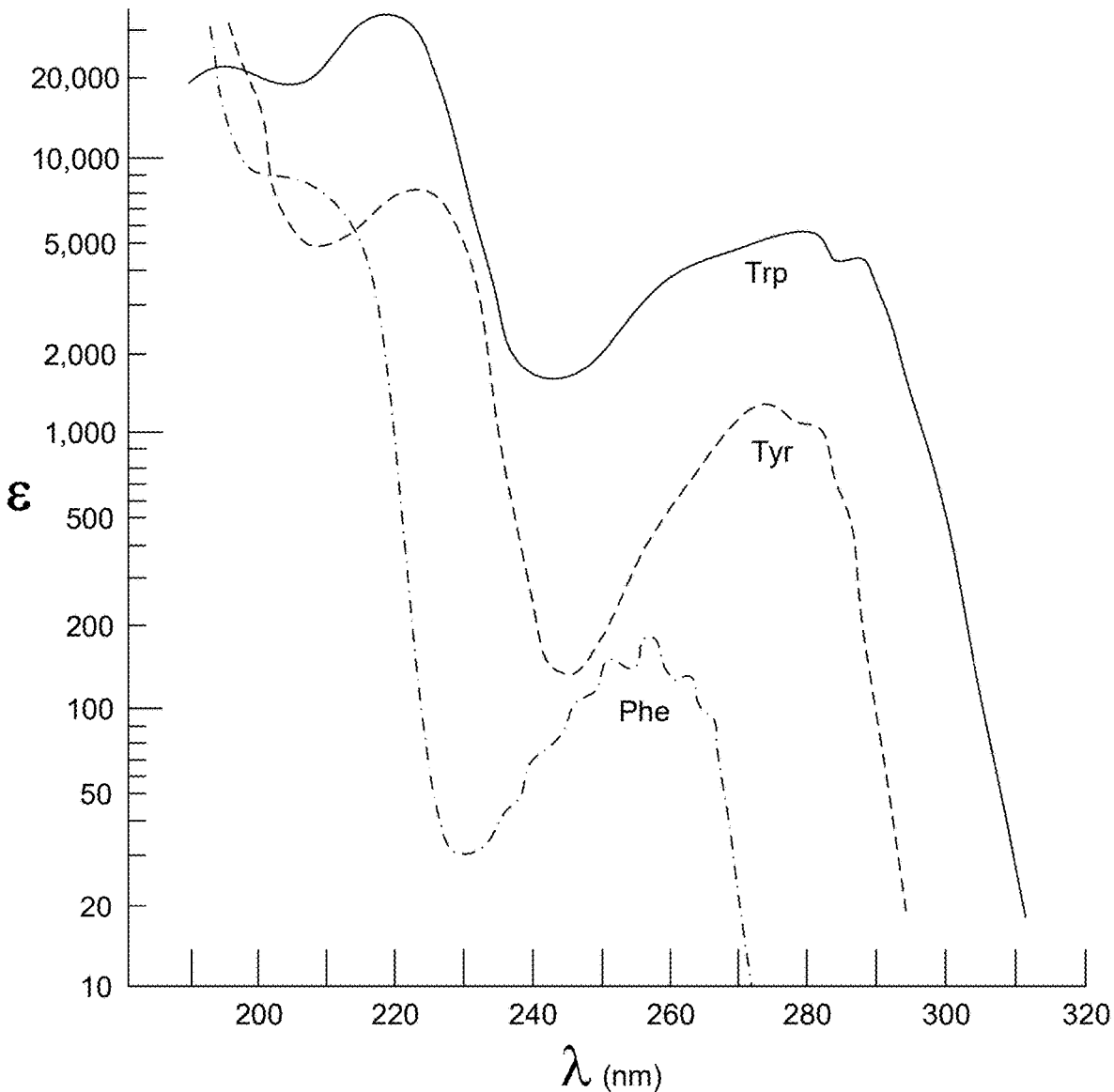
FIG. 14 is a graph illustrating the spectra of Trp, Tyr, and Phe as a function of the wavelength of the irradiating source.

Another possible source of information is the "backbone"
of a protein. A protein backbone's UV absorbance may
generate a weak emission component of approximately
1/200-1/500 the strength of Tryptophan. Since every amino
acid (AA) in a protein contributes to the emitted fluores-
cence, this can cause a split in the detected spectra into 3 or
5 groups. These readings can give insight into the length of
the protein chain, an estimate of the size of the protein
molecule itself. This potentially removes the need for size
binning of proteins in microfluidics, thus making an embodi-
ment of the disclosed device less expensive to manufacture.
The reader is referred to FIG. 14 illustrating the spectra of
Trp, Tyr, and Phe as a function of the wavelength of the
irradiating source.

Protein Detection/Identification Through UV Spectroscopy

In some cases, additional identifying information may be
provided by less common but useful sources of organic
molecule UV emission such as (for example) Carbonyl-
based blue autofluorescence and/or the UV signal formed in
protein aggregates.

In general, the UV-induced "signature" or spectrum of a
protein is determined in large part by one or more of the
following contributions:

Tryptophan absorption and emission spectra: Selectively
exciting tryptophan at its peak absorption in a protein
provides a readout signal that may be used to infer the
number of tryptophan in a protein sample. The tryptophan emission spectrum peak shifts based on the three-
dimensional conformation of proteins, and thus the
emission spectrum will add extra information about
type of tryptophan in a protein;

Tyrosine absorption and emission spectra: Selectively
exciting tyrosine at its peak absorption in proteins
provides a readout signal that may be used to infer the
number of tyrosine in a protein;

Phenylalanine absorption and emission spectra: Selec-
tively exciting phenylalanine at its peak absorption in
protein provides a readout signal that may be used to
infer the number of phenylalanine a in protein;

There may be a minor contribution from Histidine absorp-
tion and emission spectra;

Cysteine absorption spectra;

Power dependence of the fluorescence signal provides
information about the radiative and nonradiative con-
stant of a protein;

UV Spectral dependence on three-dimensional morpholo-
gies and protein sequence arrangement provides indi-
cations of the physical structure of a protein.

The decay curve of a protein's UV spectra upon first
excitation may assist in identification; Fluorescence decay
profiles are measured after UV excitation to enhance protein
identification. Proteins exhibit characteristic lifetimes influ-
enced by amino acid composition, environment, and con-
formation. In some embodiments, decay curves are collected
at multiple excitation wavelengths to provide complemen-
tary temporal signatures. These are analyzed alongside
steady-state spectra, thereby improving differentiation of
proteins using machine learning models.

UV spectra may also depend on the number of different
aromatic amino acids and the interaction of amino acids with
each other; for example, tyrosine quenches the tryptophan
emission if they are close to each other.

Nanophotonic and Optical Enhancement of Protein Emis-
sion

In the context of this disclosure, Nanophotonic structures
are nanostructures with optical properties that enhance the
light in their vicinity and may also modify the emission
properties of analytes. In this regard, recent studies have
made significant advancements in the field of UV autofluo-
rescence of proteins that operate to enhance the photosta-
bility and sensitivity of protein autofluorescence.

In some embodiments, and as part of investigating the
spectral properties of UV irradiated proteins in biofluids or
other samples, the inventors implemented and evaluated
different types of nanophotonic structures. These structures
ranged from a simple Nano Aperture (such as a hole in a
metallic film) to more advanced optical antennae (such as
Bowtie or Yagi-Uda antennas). The optimal nanostructure
for measurement of a specific sample may depend on one or
more of the analyte concentration, emission characteristics,
and quantum yields in response to irradiation. An optical
simulation may be performed to optimize the structures
using maxwell solver software such as COMSOL or Lumeri-
cal.

Protein Detection/Identification Through UV Spectroscopy

In some embodiments, the hardware elements, structures,
modules, or components of an embodiment in the form of a
device or system may include one or more of:

UV Substrate Module

This may comprise a nanophotonic-microfluidic substrate
that enhances the UV signal emitted by an irradiated protein.
In one embodiment, this substrate is equipped with nano-
structures to increase quantum yield and micro-nanochan-
nels for segregating biomarkers by their different molecular weights. A substrate may be constructed from a material such as Aluminum or Rhodium on a quartz base, thereby providing a durable and effective medium for UV light interaction. In one embodiment, the nanophotonic structures may comprise nano-wells which are small enclosures patterned onto the surface of the substrate using lithography or other semiconductor processing techniques. As mentioned, by restricting the volume of the molecules being irradiated, the number of molecules being sampled remains small, which assists in more efficient identification of a protein. To maintain or achieve such small numbers of molecules, techniques that restrict diffusion may be used, such as increasing fluid viscosity with a non-photonic interfering compound.

Illumination Module

May operate over a range of UV wavelengths (180-300 nm) for excitation of a protein and be sourced from lasers or LEDs. Features preferably include adjustable excitation powers and a pulsing mechanism to reduce photo-damage and photo-bleaching, thus maintaining the integrity of the biomarkers during irradiation and analysis.

Signal Collection Module

Incorporates optical elements and systems including one or more lenses, dichroic mirrors, or holographic elements to more accurately direct and analyze the fluorescence emitted from the sample after interaction with the substrate. Configurations vary from a single large-area spectrometer to multiple miniaturized spectrometers operating in parallel, enhancing the system's capability to analyze multiple samples simultaneously. As non-limiting examples, a spectrometer may be fabricated from a CMOS device or a CCD.

AI Algorithm

In some embodiments, the disclosed system, apparatus, or device may incorporate an integrated spectroscopy algorithm that employs deep neural network-machine learning (DNN-ML) techniques to identify a biomarker based on its collected UV fluorescence. As disclosed, embodiments utilize UV excitation of a sample to distinguish biomarkers based on the unique autofluorescence characteristics of amino acids such as Tryptophan, Tyrosine, and Phenylalanine. While the disclosed algorithm may be trained on single-molecule data, it may also be applied for purposes of multi-molecule analysis. In one embodiment, such an approach may integrate AlphaFold to incorporate biomarker structural information into a high (er)-dimensional dataset, encompassing both hyperspectral spectra and molecular structures.

Algorithm Framework

Incorporates deep learning and machine learning algorithms trained on extensive datasets of UV spectra. As described, the training datasets may be constructed from multiple samples of known proteins and/or accessing spectra available from other investigations.

Spectral Analysis

Embodiments may apply spectral unmixing techniques to resolve complex biological signals into quantifiable data. The unmixing may be performed by a trained model or applicable signal processing techniques.

Data Integration and Analysis

Solved protein structures from Protein Data Bank or AlphaFold may be used to predict and refine the spectral profiles of individual proteins, thereby improving the quality of the reference dataset and enhancing the accuracy of biomarker identification during spectral unmixing. Embodiments may also use a machine learning model trained to generate excitation/emission spectral signature based on structural data. Such a model can be run in both directions, enabling identification of proteins that have not previously been empirically or experimentally characterized (this capability has been demonstrated with Green Fluorescent protein).

A non-limiting example of a workflow for using an embodiment to develop a reference dataset of protein spectra and subsequently to use the dataset to identify one or more proteins in a sample is as follows:

Assume a mixture with different proteins where (as a non-limiting example) 5-7 proteins have concentration in the range of uM to nM and exhibit UV autofluorescence. Further, different proteins are expected to have different numbers of Tyr, Phe and Trp amino acids;

Once excited by 295 nm light (thereby selectively exciting Trp), and further with 280 and 200 nm for Tyr and Phe respectively, the sample will provide three different emission spectra;

As part of the data collection, vary the irradiating source power at each wavelength by (as a non-limiting example) 5 points, to generate 5*3=15 different spectra. It is known that different proteins (and depending upon their size and conformation) have different saturation emission signals. Thus, when varying the power, the signal intensity may change differently, where a point of differentiation is linear slope as well as peak saturation power; that is, the disclosed process uses a power to emission intensity curve as the readout to differentiate between proteins.

On the data processing side, it is important to recognize that one knows a priori the proteins or analytes being detected when compiling the reference data of multiple samples, and one may also have an idea about the possible concentration range of these analytes in solution. In this regard, there is pre-trained data from protein molecules which is used to deconvolute individual contributions from a sample mixture. The a priori information representing the signal from a single molecule of protein is collected and stored in a cloud-based platform.

The disclosed and/or described approach trains an AI algorithm/model for spectral unmixing using the following techniques:

Collect purified protein spectra with the different irradiation conditions mentioned above;

Generate training data: Machine learning (ML) to create spectra of an artificial mixture of different proteins with different concentration and compare it with experimental results of UV spectra of those mixtures (a form of validating the approach);

Use the collected data to train an algorithm/model to spectrally unmix a spectrum to isolate/identify the individual contributions;

A result is an algorithm which is trained with purified protein spectra as well as different mixtures of the proteins;

Excitation can be performed across a range of wavelengths or at specific wavelengths selected to preferentially excite distinct chromophore types within a structure. Hyper-spectral data consists of excitation spectra collected at multiple wavelengths, forming a tensor that captures numerous emission spectra corresponding to different excitations. These emission spectra vary and, if analyzed independently, may lead to inconsistent deconvolution results. To address this, the inventors trained a hybrid model that assigns weights to each excitation wavelength, enabling the scoring of the different spectra. Deconvolving such data may require a deep neural network capable of accurately computing and applying the appropriate weights to each deconvolution output. In order to train such a model, the inventors used multiple proteins exhibiting a diversity of F, W, Y counts and contexts;

For the model to work efficiently, it is desirable that the collected data exhibits single molecule resolution, and a relatively low number of molecules detected per volume. It is important to do these evaluations or checks multiple times to create a clear and reliable statistical picture;

This aspect is where the hardware used in an embodiment plays a crucial role, as the nanophotonic substrate provides optical enhancement capabilities (acting in one sense as a photomultiplier) to enable the device to perform single molecule spectroscopy as well as provide a sub-diffraction detection volume;

The set of (or single) or array of such nanophotonic structures are mapped onto several pixels of a CMOS spectrometer and act as a single measurement unit; if one has a 20 Megapixel CMOS chip and uses 10 pixels to map a signal from a group of nanophotonic structures (where the size of the group will depend on the total signal and CMOS sensitivity), one can perform 2 million measurements at a time. This results in a large array of nanostructures (in the range of millions in the substrate), with each nanostructure functioning as a detection unit;

Note that the disclosed approach is not emission detecting at just one point; instead, an embodiment is capable of simultaneously detecting 1,000's of emitted spectra at the same time. During the detection process, proteins are continually diffusing into each detection nanostructure (such as a nano-well) and being excited and emitting a detectable emission spectrum and then diffusing out. This situation enables making millions of readings over the course of the detection process, with each individual spectral signature then mapped to a distinct protein;

On a timescale of 30 sec (i.e., a range from 10 to 60 sec) acquisition for each input, for 15 different inputs, the result is a 7.5 min acquisition time in which the device will collect 2 million measurements (thus, a single measurement happens during a microsecond range).

FIG. 2 is a diagram illustrating elements or components that may be present in a computing device, apparatus, or system 200 configured to implement a method, process, function, or operation in accordance with some embodiments. In some embodiments, the disclosed and/or described system and methods may be implemented in the form of an apparatus that includes a processing element, and a set of computer-executable instructions stored in (or on) a non-transitory computer-readable medium. The executable instructions may be part of a software application and arranged into a software architecture.

In general, an embodiment of the disclosure may be implemented using a set of software instructions that are executed by a suitably programmed processing element (such as a GPU, TPU, CPU, microprocessor, processor, controller, state machine, or other form of computing device, as examples). In a complex application or system such instructions are typically arranged into "modules" with each such module typically performing a specific task, process, function, or operation. The entire set of modules may be controlled or coordinated in their operation by an operating system (OS) or other form of organizational platform.

Modules and/or sub-modules may include a suitable computer-executable code or set of instructions (e.g., as would be executed by a suitably programmed processor, microprocessor, CPU, or GPU), such as computer-executable code corresponding to a programming language. For example, programming language source code may be compiled into computer-executable code. Alternatively, or in addition, the programming language may be an interpreted programming language such as a scripting language.

As shown in FIG. 2, system 200 may represent an apparatus or other form of computing or data processing device. Modules 202 each contain a set of executable instructions, where when the set of instructions are executed by a suitable electronic processor (such as that indicated in the figure by "Physical Processor(s) 230"), system (or server, platform, or device) 200 operates to perform a specific process, operation, function, or method.

Modules 202 may contain one or more sets of executable instructions for performing a method or function disclosed herein and/or described with reference to the Figures, and the descriptions of the functions and operations provided in the specification. The modules may include those illustrated but may also include a greater number or fewer number than those illustrated. Further, the modules and the set of computer-executable instructions that are contained in the modules may be executed by the same processor or by more than a single processor.

Modules 202 are stored in a (non-transitory) memory 220, which typically includes an Operating System module 204 that contains instructions used (among other functions) to access and control the execution of the instructions contained in other modules. The modules 202 in memory 220 are accessed for purposes of transferring data and executing instructions by use of a "bus" or communications line 218, which also serves to permit processor(s) 230 to communicate with the modules for purposes of accessing and executing a set of instructions.

Bus or communications line 218 also permits processor(s) 230 to interact with other elements of system 200, such as input or output devices 222, communications elements 224 for exchanging data and information with devices external to system 200, and additional memory devices 226.

As a non-limiting example, an embodiment may be in the form of a hand-held or portable device into which a sample may be placed for analysis. The device may include the following elements, components, processes, or functions:

A nanophotonic substrate;

An adjustable source of UV irradiation;

One or more optical elements to focus, direct, or control the UV radiation generated by the source onto the sample and to direct the fluorescence generated by the proteins in the sample onto a detector;

A detector to receive the fluorescence generated by the proteins in the sample, and in response to generate electrical signals indicative of the spectra or spectrum of the fluorescence;

A processor executing a set of instructions or form of trained model that operates to "predict" or infer the protein or proteins in the sample based on the signals generated by the detector; and A user interface that presents an identification of the predicted or inferred proteins to the user.

In one embodiment, the device may communicate and exchange data with a remote platform or server. The platform or server may include a datastore (such as a memory) which contains a dataset comprising spectra or spectrum of multiple proteins with an indicator of the protein corresponding to a spectra or spectrum. The datastore may be used to train or update a model, with the updated model accessed by the device and/or transferred to the device's own memory. Each device (or user or other entity) may correspond to its own "account" on the platform, which may be implemented as a form of SaaS or multi-tenant platform or service.

Each module 202 or sub-module may correspond to a specific function, method, process, or operation that is implemented by execution of the instructions contained in the module or sub-module. That is, each module or sub-module may contain computer-executable instructions that when executed by a programmed processor or processors cause the processor or processors (or a device or devices in which they are contained) to perform a specific function, method, process, or operation. Such function, method, process, or operation may include those used to implement one or more aspects of the disclosed and/or described system and methods, such as to perform or control the performance of a process, function, or operation to:

Develop a database of measurements of UV autofluorescence for multiple proteins, where the measurements are conducted at multiple wavelengths and/or power of incident UV excitation/radiation (as suggested by module 206);

In one embodiment, this may include using datasets in the database to train a model to identify (i.e., infer or predict) a protein responsible for generating a collected spectrum;

The spectra or spectrum corresponding to each irradiated protein may be obtained from measurements of known proteins using the disclosed measurement components and processes, and/or from previously investigated spectra of one or more proteins or combinations of proteins;

Recognize or respond to placement of a sample on a substrate, where the substrate is configured to enhance a signal generated by a protein in response to irradiation (as suggested by module 208);

Irradiate/Excite the sample by a UV source at one or more wavelengths and/or one or more powers (as suggested by module 210);

In most cases, the sample will be irradiated with a set of wavelengths and powers that correspond to those used to collect the reference data in the database;

Collect and direct/focus the generated photons from the substrate by suitable optics or optical elements (such as quartz optics, lenses, or holograms) onto a detector (as suggested by module 212);

Detect the directed photons by the detector, such as a CMOS spectrometer (as suggested by module 214);

Process the signal(s) output by the spectrometer using a trained model (as suggested by module 216);

In one embodiment, the trained model or an updated version may be accessed by communication with a remote server or platform; and Output an indicator of the identified protein or proteins in the biofluid sample and the corresponding quantity based on the output of the trained model (as suggested by module 217);

In one embodiment, the trained model may perform spectral unmixing (decomposition) followed by data processing to prepare the signal(s) from the detector for identification as being produced by a specific protein;

In one embodiment, the trained model may function as a classifier that operates to compare a spectra or spectrum of a sample to a dataset containing previously collected spectra or spectrums with an indication of the corresponding protein responsible for generating the spectra or spectrum.

FIGS. 3-13 are diagrams illustrating arrangements of components or elements that may be used to implement an embodiment of the disclosed and/or described system and methods. As should be evident, there are multiple ways of implementing one or more of the components or processes disclosed, with the implementation chosen possibly depending on the environment in which the measurement is conducted, the type or types of proteins expected in a sample, the sample conditions or composition, or the type or range of data it is desired to collect, as non-limiting examples.

Figure 3:
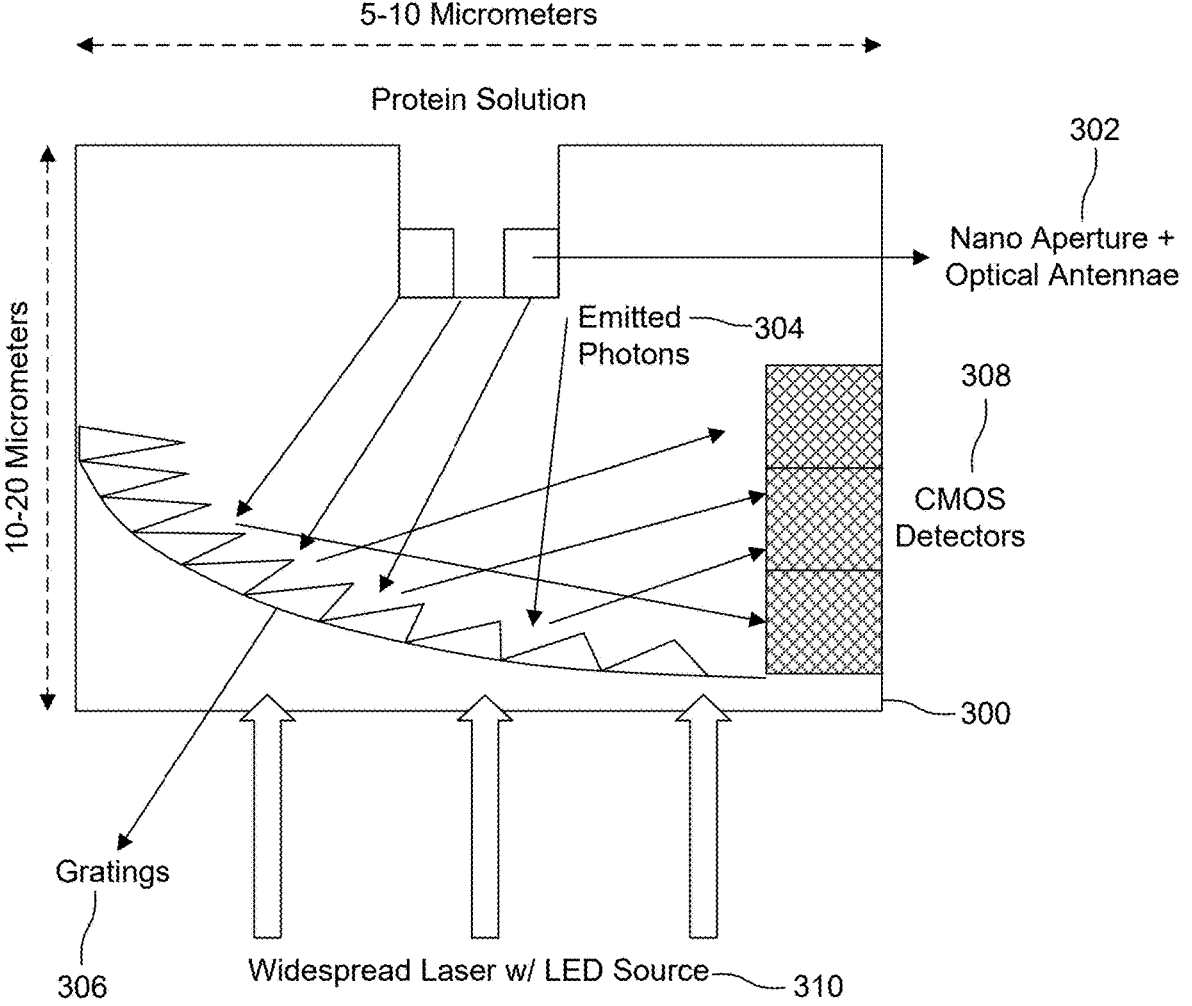
FIGS. 3-13 are diagrams illustrating arrangements of components or elements that may be used to implement an embodiment of the disclosed and/or described system and methods.

FIG. 3 is a diagram illustrating a single detection cell embodiment 300. The cell 300 contains a zero-mode waveguide or other nanophotonic structure 302 (illustrated as "Nano Aperture and Optical Antennae" in the figure) that enhances protein or biomolecule signals (i.e., photons 304 generated as a result of being exposed to UV radiation). The unit is integrated with a micron (um) size diffractive element 306 that redirects the emitted photons, and a CMOS or optical detection pixel 308 that responds to the detected photons to generate electrical signals corresponding to components of a spectrum. A source of irradiation 310 (such as a laser or LED, a micro-laser or micro-LED) is dedicated to each cell or may be fed through a waveguide (not shown) using a single source. For multiple wavelength irradiation and emission capture one can use different cells, such as a group of four cells forming one detection unit. In this configuration, the four cells would typically correspond to four different wavelengths of illumination, for example 220-235, 250-255, 265-275, 285-295 nm.

Figure 4:
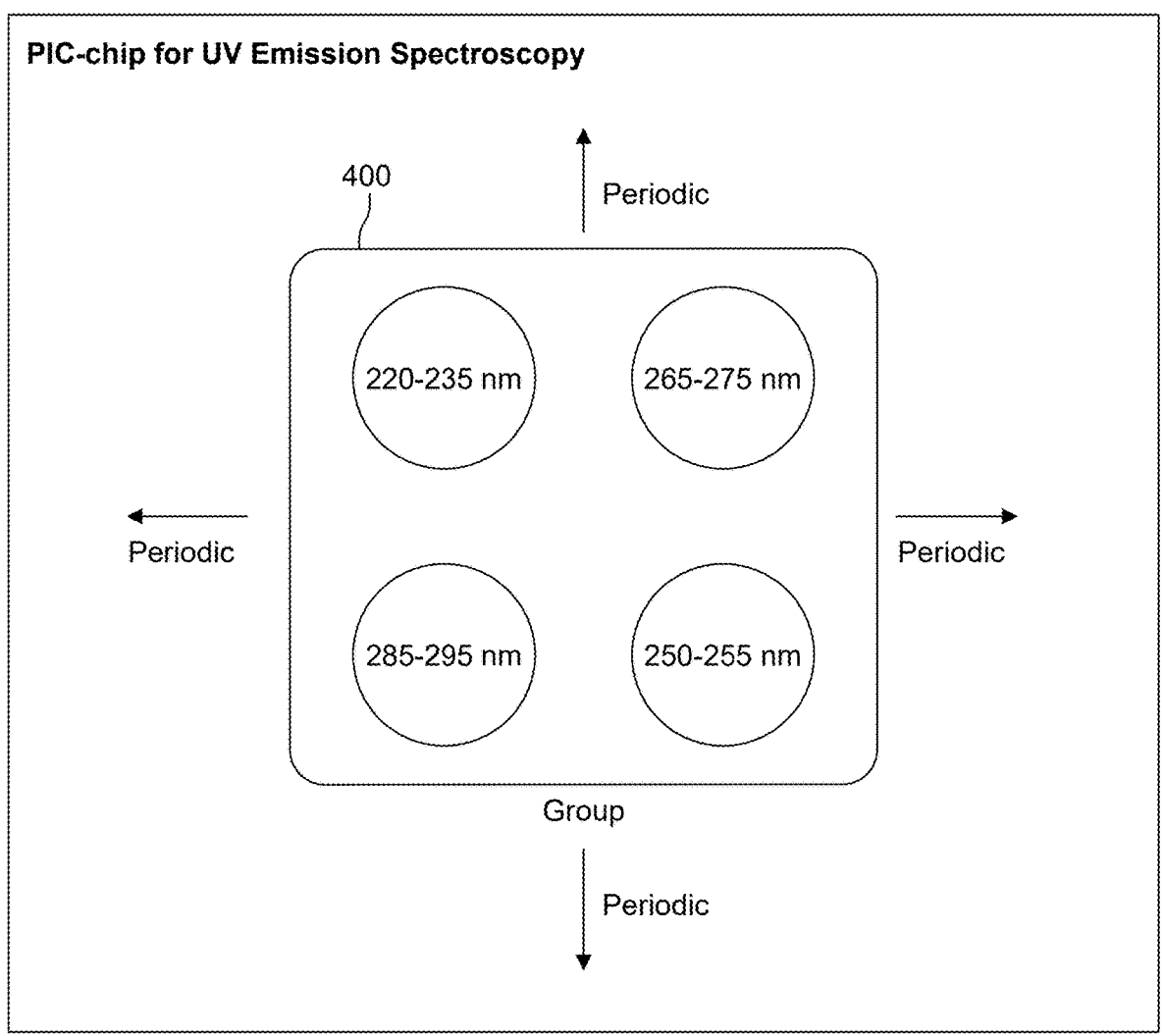

FIG. 4 is a diagram illustrating a design for a four-cell detection unit or group 400 (which may also be referred to as a photonics integrated chip or PIC) that is capable of detecting UV fluorescence from an irradiated sample at four distinct wavelength bands (illustrated as 220-235 nm, 250-255 nm, 265-275 nm, and 285-295 nm, as non-limiting examples). As indicated in the figure, the detection unit is duplicated across a surface to form an "array" of such detectors or units.

Figure 5:
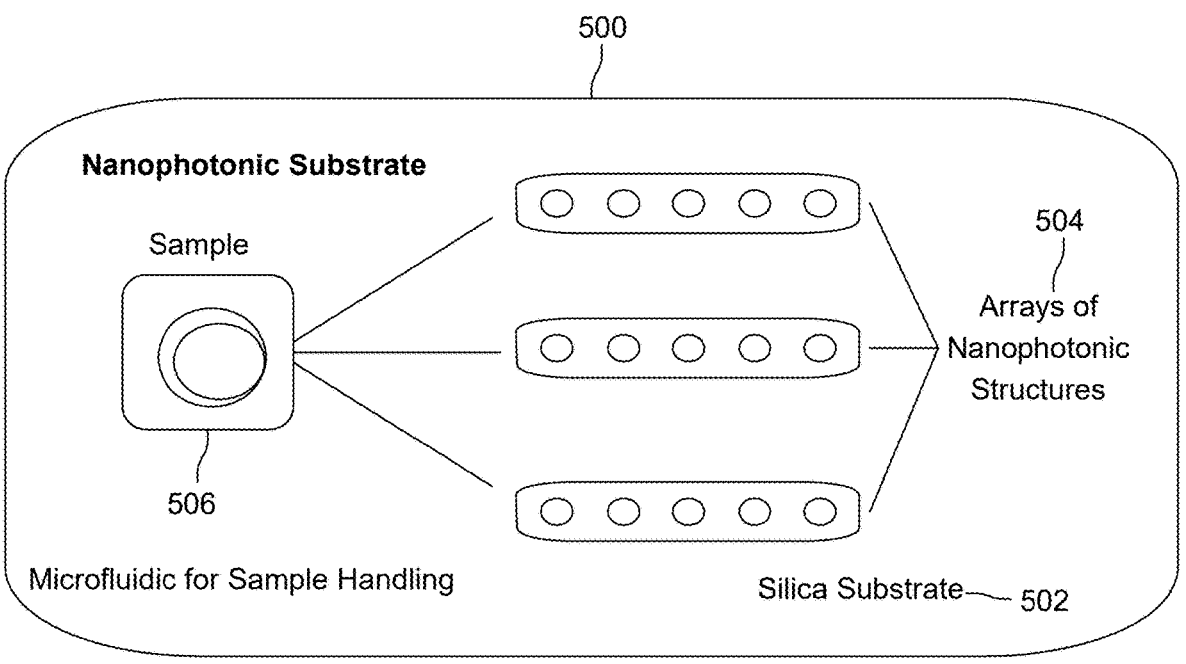

FIG. 5 is a diagram illustrating an example of a nanophotonic substrate 500 that may be used to implement an embodiment of the disclosure. In one embodiment, the nanophotonic substrate consists of quartz material as a base substrate 502 (or other UV transmissive material) with nanophotonic 504 and microfluidic 506 units. The microfluidic system consists of units to handle samples and divide the solution based on size of an analyte (as an example). The liquid is then directed toward the arrays of nanostructures. As non-limiting examples, the nanostructure can be a metallic nanoaperture, an optical nanoantenna, or other optical system that enhances the signal from proteins and other analytes.

Figure 6:
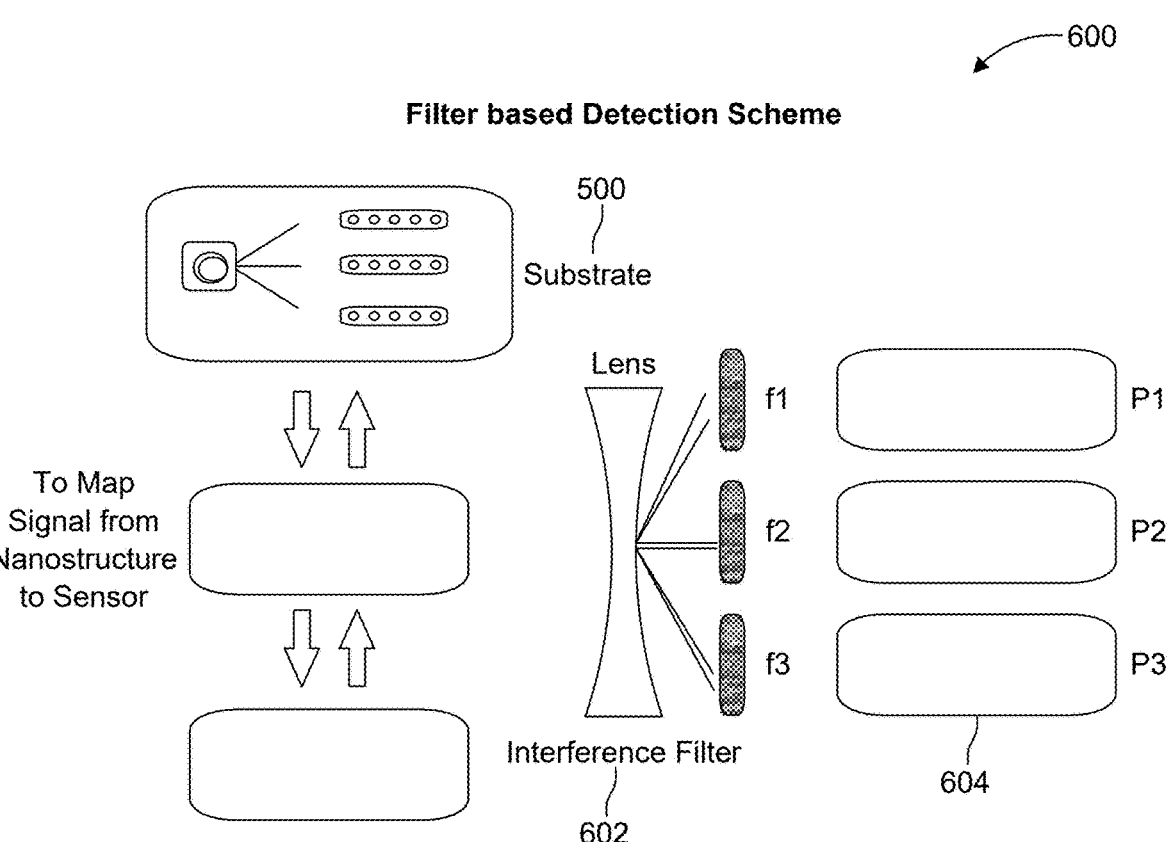

FIG. 6 is a diagram illustrating an example of a filter-based detection approach 600 using one or more filters 602 (identified as f1, f2, f3 in the figure) and a photodiode 604 (identified as P1, P2, and P3 in the figure) as a detection mechanism (instead of the CMOS chip or other form of spectrometer), and that may be used to implement an embodiment of the disclosure. The filter is an interference filter with a passband specific to a given analyte or biomarkers, and the intensity recorded at each photodiode is specific to the analyte. This configuration may help in discerning the concentration of one or more analytes in a solution.

Figure 7:
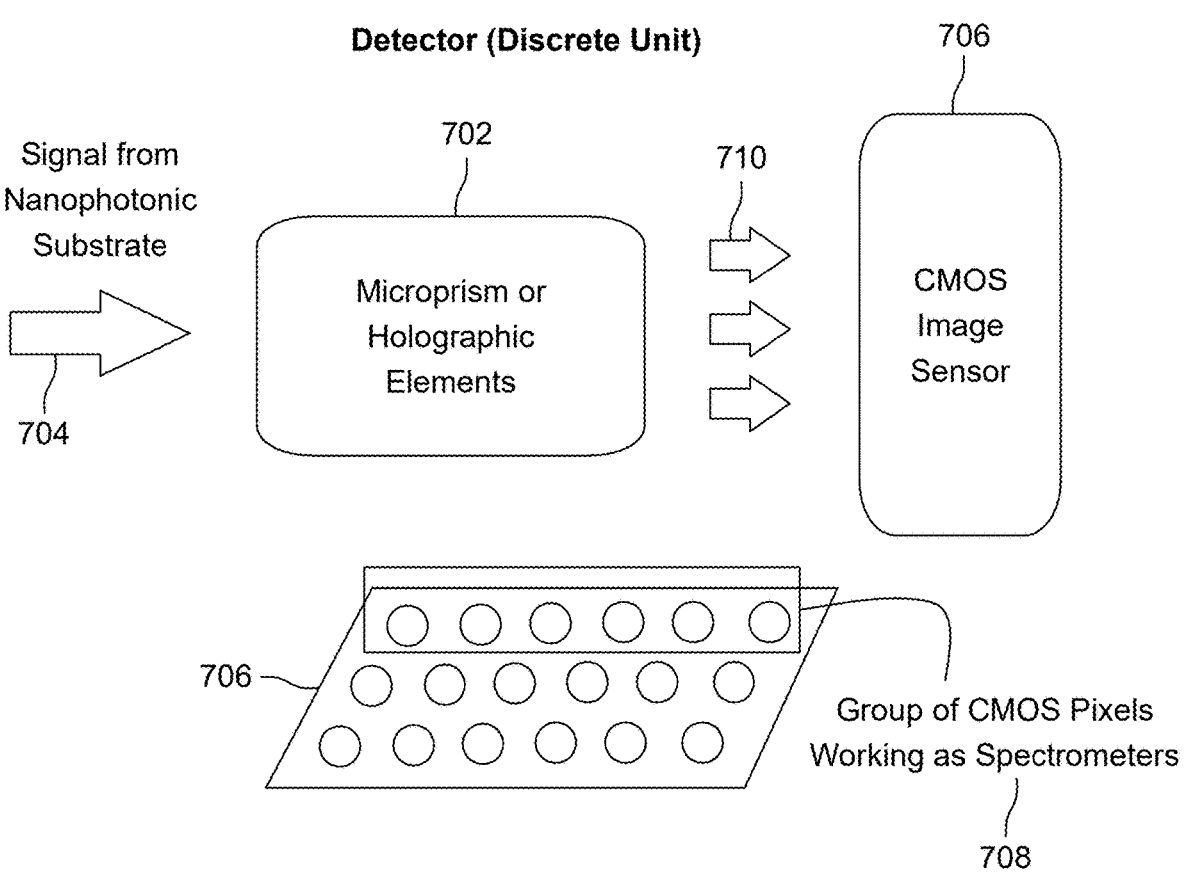

FIG. 7 is a diagram illustrating a detector that may be used to implement an embodiment of the disclosure. In this example embodiment, a microprism or holographic elements 702 may be used to direct the photons/signals generated by the nanophotonic substrate 704 to a detector, such as the illustrated CMOS image sensor 706. The image sensor 706 is a set of CMOS pixels 708 that function as spectrometers. The detector consists of an element 702 to disperse the signal coming from the nanophotonic substrate onto a CMOS image sensor 706. As shown, non-limiting examples of the optical element can be a microprism, gratings or holographic elements 702 together with a lens (as suggested by 710) to map the signal from the substrate onto pixels of the CMOS image sensor.

Figure 8:
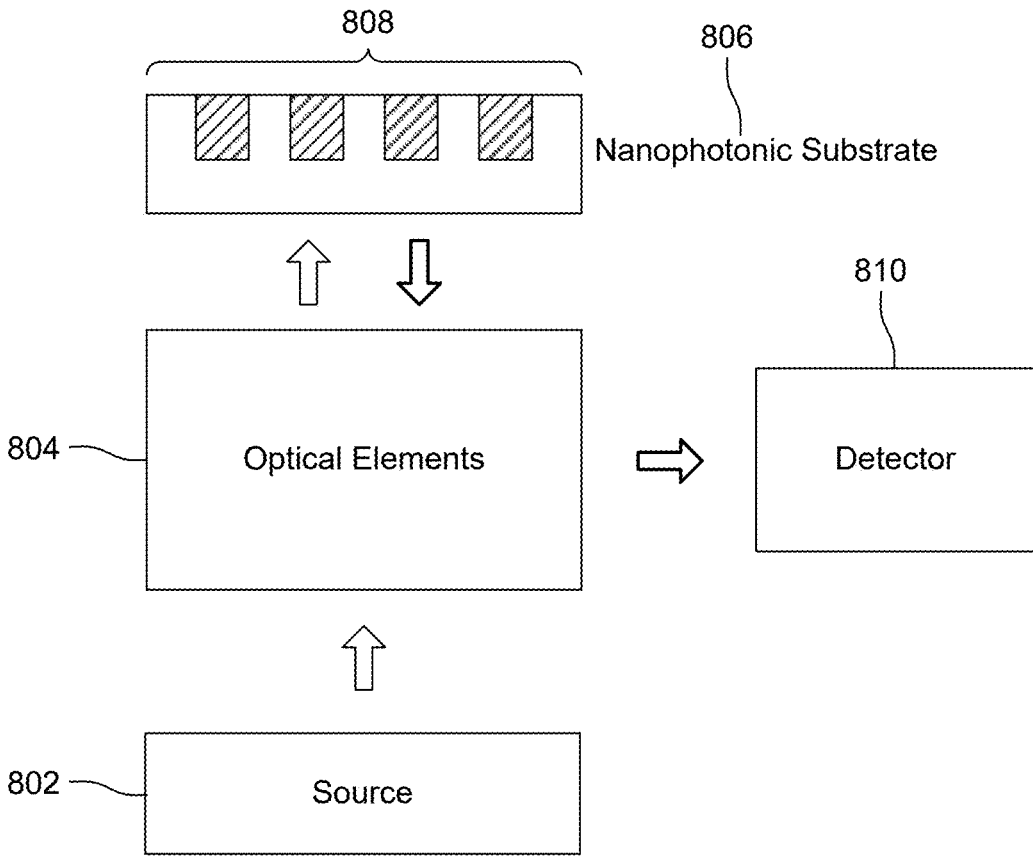

FIG. 8 is a diagram illustrating the primary components of an embodiment of the disclosed and/or described device for determining the presence of one or more biomarkers in a solution. As shown in the figure, a basic configuration of the device consists of a source 802 (e.g., LED or laser, that is continuous or pulsed) with a capability to generate photons at multiple wavelengths and with a range of power and duty cycle. The optical element 804 is a combiner which directs the light from the source to illuminate a sample solution 808 (as suggested by the upward facing arrow) placed on a nanophotonic substrate 806 and then directs photons generated by the fluorescence of the proteins in the sample signal (as suggested by the downward facing arrow) to the detector 810.

In one embodiment, the nanophotonic substrate is a unit consisting of microfluidic and nanophotonic structures. The microfluidic structures contain and transfer the sample solution and the nanophotonic structures enhance the signal from proteins and other analytes of interest in the sample solution. The detector consists of optical elements to disperse the light coming from the nanostructures and operate to map the signals (photons) from the nanophotonic structures to pixels of a CMOS image sensor which operates as a spectrometer.

Figure 9:
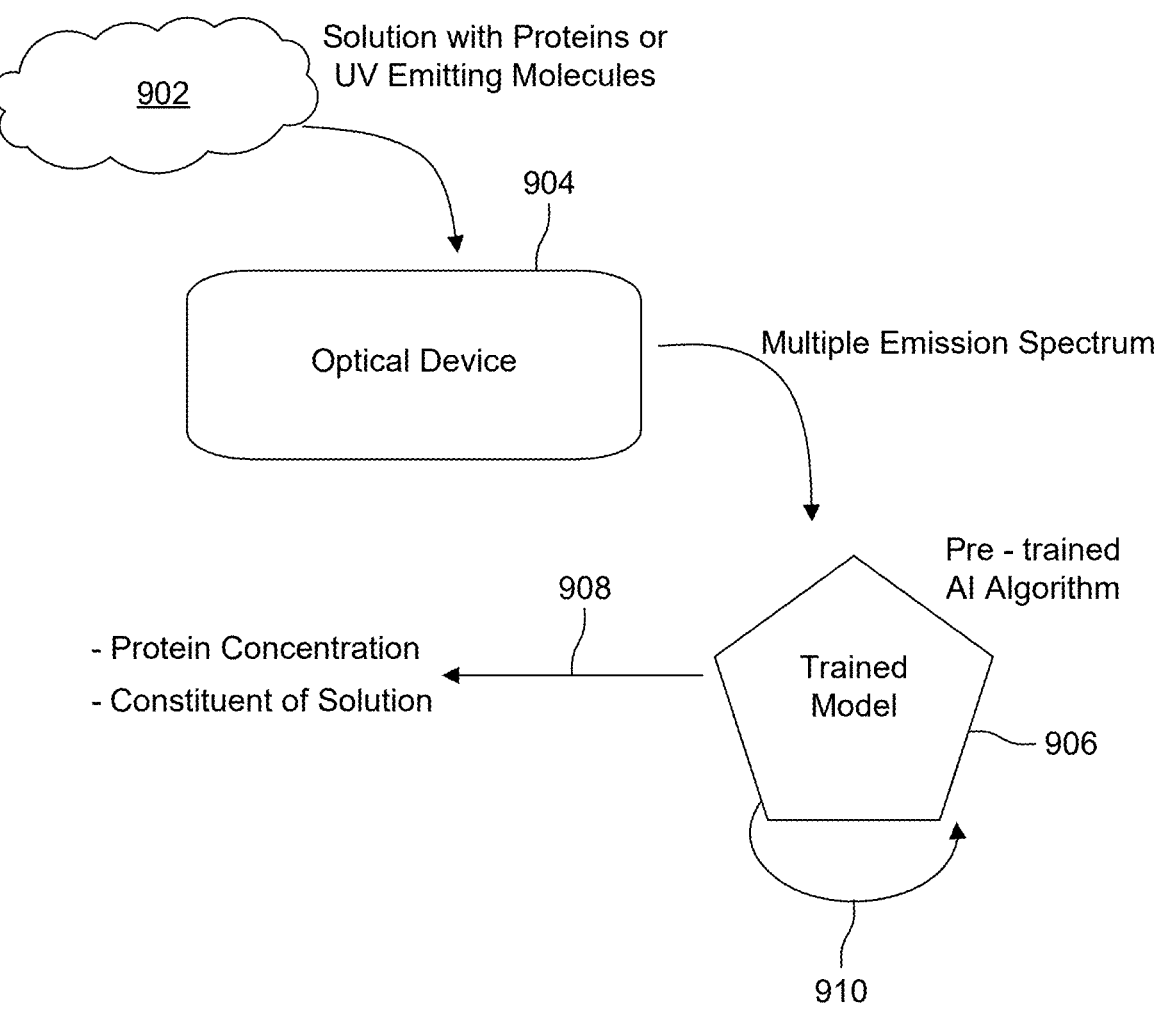

FIG. 9 is a diagram illustrating the primary components and operations of an embodiment of the disclosed and/or described device for determining the presence of one or more biomarkers in a solution. As shown in the figure, an embodiment and use case consists of an input sample 902 containing a UV fluorescent analyte that is introduced to the optical device 904 described with reference to the previous figures. The optical device 904 transfers data and communicates with a trained model 906 which may be deployed "in the cloud" along with a proprietary reference dataset. The output from the model 908 is a detailed analysis of the solution to in the form of identified proteins and their relative concentrations in the solution. As suggested by the figure, the output data from the model may be used to update the model 910 by providing additional training or validation data.

Figure 10:
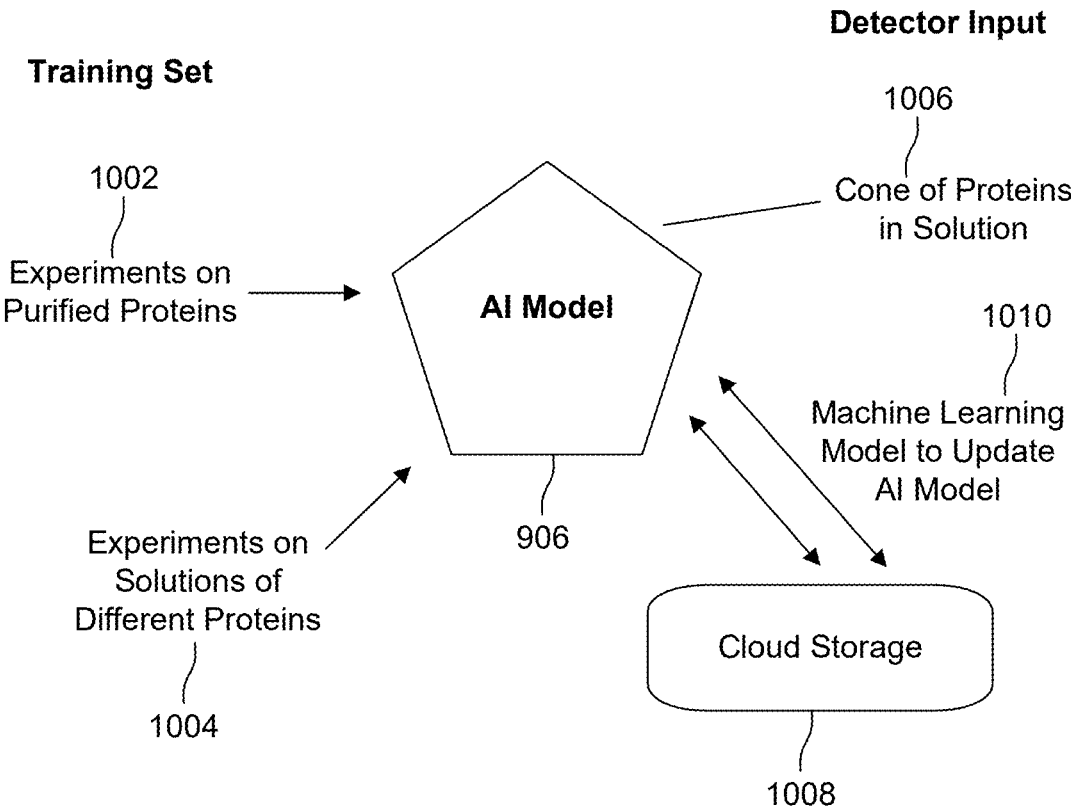

FIG. 10 is a diagram illustrating the training and use of the model described with reference to FIG. 9. As shown in the figure, in one embodiment, the training algorithm is applied to a dataset generated from experiments 1002 and 1004 that are used to train the model 906. Models can be made using a Deep Neural Network or other machine learning algorithm. Once trained by the dataset the model is deployed to interpret the signal from the detector/spectrometer and identify the protein or proteins in the sample 1006.

The model may be resident "in the cloud" 1008 (such as by being available through a server that is part of a multi-tenant or SaaS platform) to allow for continued training of the model after initial deployment 1010. The updated or refined models may then be accessed and/or downloaded to the device for use in the field.

Figure 11:
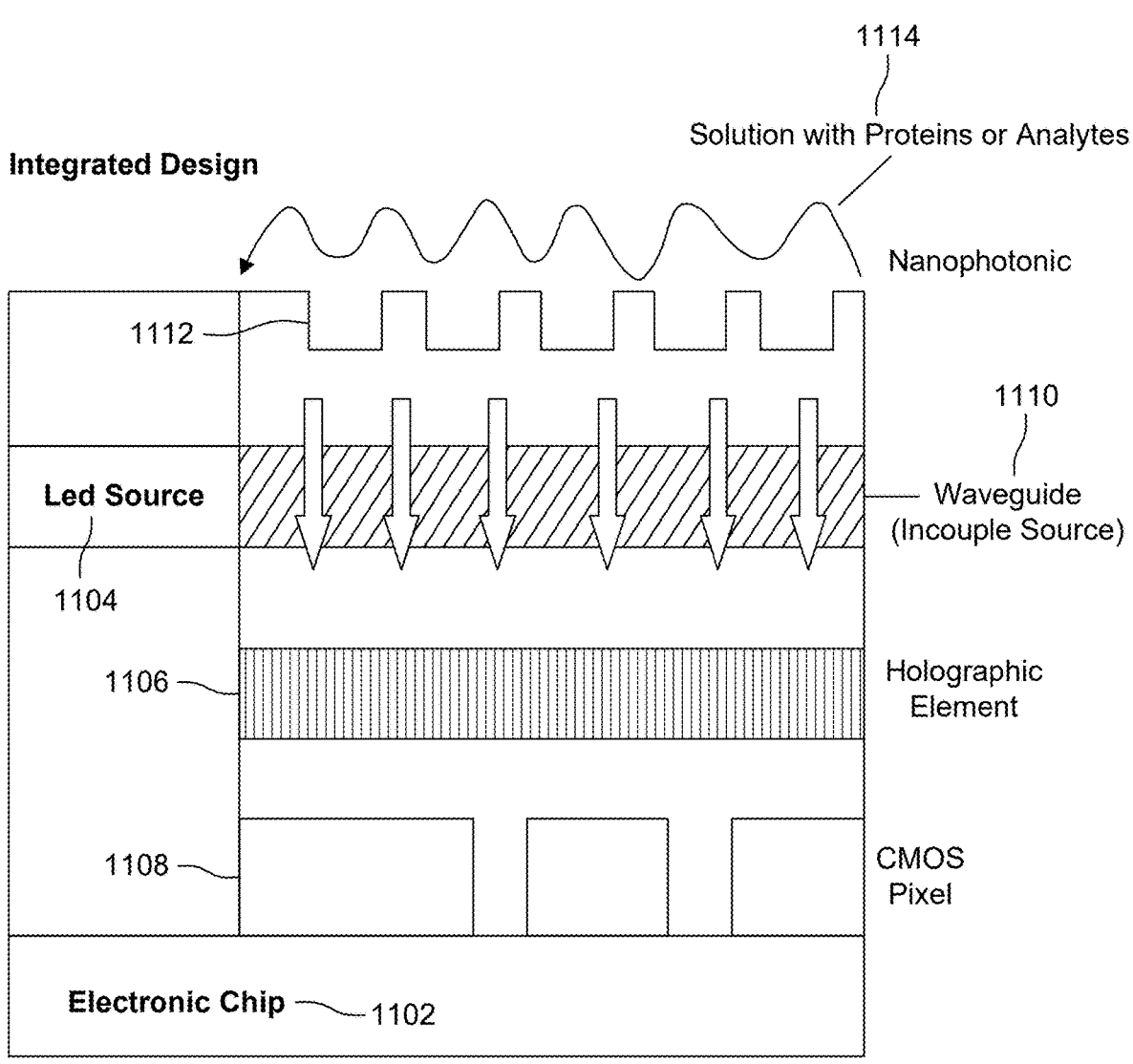

FIG. 11 is a diagram illustrating an embodiment where the disclosed device includes an integrated photonic chip 1102 built on a CMOS architecture. As shown in the figure, the discrete units (i.e., source 1104, optical elements 1106, and detectors 1108) are integrated in one block, and the power electronics operates to drive both the CMOS chip and LED source. A waveguide 1110 is used to direct or couple photons from the LED source 1104 (e.g., a nano-laser, micro laser, or micro-LED) to the holographic elements 1106. The holographic elements 1106 operate to disperse light from nanophotonic structures 1112 onto CMOS chip pixels 1108, enabling the pixels to operate as a spectrometer. The entire design shown in the figure is a single unit and there may be hundreds or thousands of such units as part of one device. Note that the arrows indicate the emitted photons from the irradiated sample solution 1114.

Figure 12:
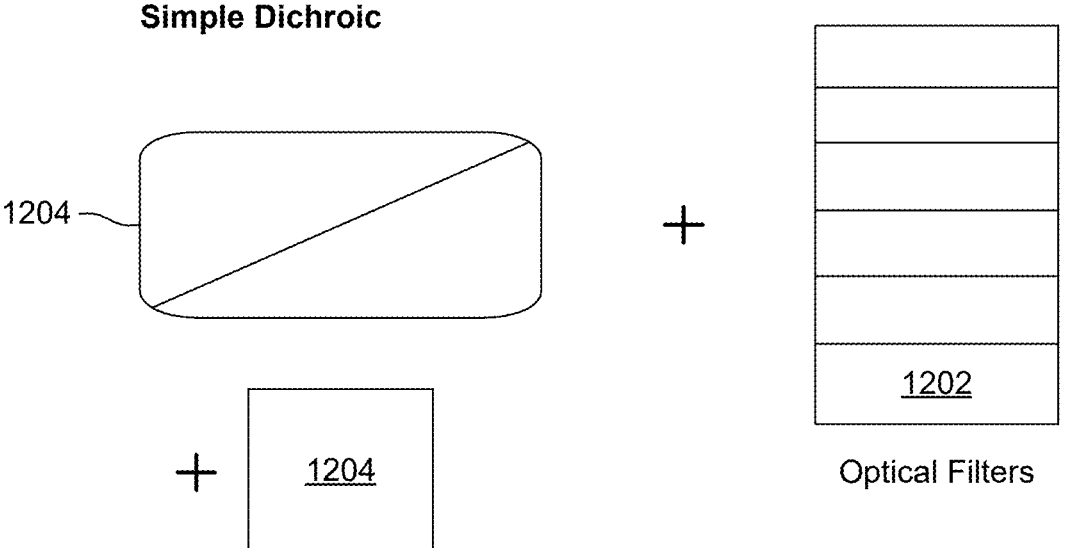

FIG. 12 is a diagram illustrating examples of optical elements that may be used to implement an embodiment of the disclosure. As suggested by the figure, the optical elements placed between the substrate, source, and detector act as a photon relay and combiner; they direct light from a source to the nanophotonic substrate to illuminate the sample and then direct the emitted fluorescence from the substrate to a detector. The optical elements may include one or more filters 1202 to prevent light from the source falling on the detector. The lens system shown 1204 is used to create a wide field illumination of the substrate.

Figure 13:
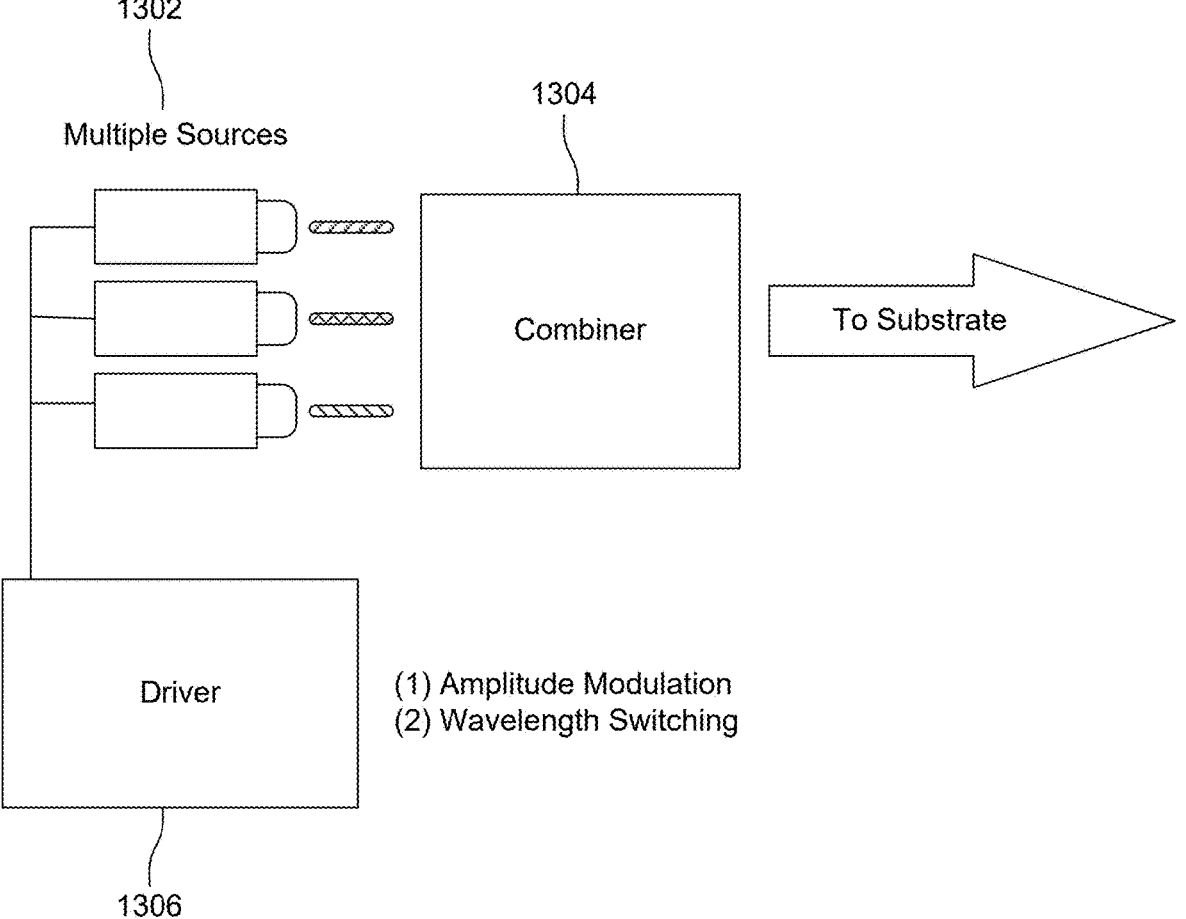

FIG. 13 is a diagram illustrating an example of a source that may be used to implement an embodiment of the disclosure. As shown in the figure, an example source may contain multiple wavelength sources 1302 that are combined or collimated 1304 to illuminate the substrate. In one embodiment, the sources are capable of generating photons having wavelengths ranging from 180 nm to 300 nm. The sources' power and duty cycle can be varied and controlled by the drivers 1306. The sources may be LEDs or Lasers and can be continuous wave or pulsed wave.

Embodiments of the disclosed and/or described method and devices provide several features and benefits not found in conventional approaches to determining the biomarkers or other constituents of a fluid. As one example, the nature of and diversity of the spectra or spectrum that can be obtained is a differentiating feature of the embodiments. Detectable or not, there is a unique spectral signal for a protein even if it has an identical or similar FWY (Phenylanaline (F), Tryptophan (W), Tyrosine (W)) ratio to another protein. This unique signature has been impossible to detect (or nearly so) using conventional approaches due to the averaging effects inherent in the solution-based sampling used by conventional approaches and devices. In contrast, by using the disclosed elements and processes, one is able to investigate a single or a few molecules at a time, and this overcomes the averaging problem and provides greater detail, thereby providing a better opportunity to detect the actual spectral signal.

As further background, there are several factors that can affect the absorbance or emission of radiation from a protein molecule:

The count and identity of the fluorescent Amino Acids-typically Phenylanaline (F), Tryptophan (W), Tyrosine (W), and possibly Histidine (H);

The spatial arrangement within the overall structure of the protein. This happens in the following ways:

Molecular interactions within a protein's structure can stabilize or destabilize the ground and/or excited state(s) producing red or blue shifts in excitation wavelengths; and Incident light on a molecule will only be absorbed by one or two favorably oriented dipoles at any one time and this leads to peak-splitting in the spectra.

Much (if not all) of these effects are averaged out when molecules are analyzed in solution. Because most protein-based spectral studies have been done in this way, this resulted in spectra that are not easily distinguished from each other.

However, by having the ability to irradiate and investigate single molecules, embodiments recapture more of the distinguishing features of these excitation/emission spectra and have the ability to use these more distinct spectral signatures to uniquely identify the proteins that generated them. Embodiments also avoid the noise from inevitable degradation products that also impact and can degrade resolution.

The preparation of a sample for irradiation may include use of one or more of the following techniques, with the specific technique or techniques used depending upon the sample and its condition:

Protein purification to filter out non-protein molecules-Hydroxyapatite to remove DNA, cleave and remove glycans, and polysaccharides;

Size exclusion chromatography to remove small molecules which can create noise in the signals;

Controlled proteolytic cleavage, that will predictably cut large proteins (that may have complex spectra) into smaller distinct domains that have more easily discernible spectra. In this case, the identification of a distinct protein may be done by combining multiple spectra into a fuller spectrum;

Sample Fractionation and/or Staging:
Instead of analyzing an entire sample at once, one can apply these techniques to achieve a staging of the signal collection process. This also allows identifying which spectra were collected at distinct stages of the overall detection process;
Non-limiting examples of this approach include:
Sample fractionation by size, pH, or affinity column;
Size exclusion fractionation to detect proteins in size-based fractions;
Isoelectric focusing-separation of proteins based on charge. Differently charged molecules can be segregated to different zones of a detection surface. These features or devices can be incorporated into a single integrated purification/fractionation/detection cassette;

Altering the chemical environment of the detection process:
By collecting spectra generated in different chemical environments, one can create a distinct signal and/or create conditions that improve or predictably alter the spectra that are collected. Non-limiting examples of this approach include:
Reagents to stabilize a protein structure such as physiological buffers, PEG;
Reagents to slow diffusion or Brownian motion, such as glycerol, a gel matrix, PEG, or colloid;
Additives or solvents to affect the absorption profile of a sample;
Changes to pH, salts, organic environments, or carbonyl paper, as these affect protein stability and motion;

Altering the sample temperature to affect protein stability and motion (the temperature may be increased or decreased during stages of a measurement);
Some proteins can be stabilized with their dedicated ligands or analogues thereof and this allows probing of these proteins at higher temperatures, indicating function of the species being interrogated;

Probing a protein structure to indicate a function of the species being probed;
For example, ANS (1-Anilinonaphthalene-8-sulfonic acid) binds hydrophobic residues and can be used to detect disturbed protein structure for a molten globule state; and Reversibly disrupting a protein structure to identify structure-based features using GdnHCL, Urea, a Urea gradient in gel, or a pH gradient.

The disclosed and/or described measurement scenarios may be applied to capture and analyze spectra under a variety of conditions and protocols, including the following non-limiting examples (which may provide additional information that can be used to identify a protein in a sample):

Temperature-Controlled UV-Based Protein Detection;
Apply a controlled heating process to a liquid sample, wherein the temperature is incrementally increased over time;
Continuously measure the UV autofluorescence signature of the proteins in the sample during the heating process;
Identify changes in the UV autofluorescence signature at specific temperature thresholds that correlate to the denaturation of different proteins, based on their distinct thermal stability; and
Determine the protein composition of the sample by analyzing the relationship between the temperature-induced changes in the UV signal and the corresponding denaturation points of the proteins;

Enhanced Protein Detection Combining UV-Autofluorescence with Amino Acid-Specific Turn-On Dyes;
Introducing into a sample a fluorogenic dye that remains substantially non-fluorescent until it binds or reacts with a specific amino acid residue of a protein;
Exciting the fluorogenic dye at an appropriate wavelength, distinct from or complementary to the wavelength used for UV autofluorescence measurements;
Detecting a secondary fluorescence signal attributable to the dye-protein interaction; and
Combining or comparing the secondary fluorescence signal with the existing UV autofluorescence data to obtain enhanced detection sensitivity and/or specificity;

Free-Flow Electrophoresis (FFE) for Protein Gradient Detection Using UV Optical Interrogation;
Introducing a liquid sample containing proteins into a free-flow electrophoresis system equipped with an optical detector;
Subjecting the liquid sample to an electric field applied across a continuous flow chamber, thereby separating proteins based on their electrophoretic mobility, which is influenced by their charge, size, and isoelectric point;
Guiding or directing the separated proteins along a flow path that starts upstream of the optical detector and passes through the detector, wherein the proteins arrive at the detector in a spatially resolved gradient based on their electrophoretic mobility;

Exposing the proteins to multi-frequency ultraviolet (UV) light as they pass through the detector, enabling interrogation of their autofluorescence or absorption spectra at different frequencies;

Using the continuous flow to carry away photobleached proteins, thereby maintaining the accuracy and sensitivity of UV detection; and Optionally adding one or more internal reference markers to the liquid sample, where the markers comprise simple dyes or molecules with known molecular weight and isoelectric point; the added markers serve as calibration points for the gradient and facilitate protein identification;

UV-Transparent Polymer Brushes or Hydrogels with Temperature-Sensitive Release (to enable trapping and releasing of proteins in a sample);

Coating a substrate, such as a micro-well or sensor surface, with a UV-transparent polymer brush or hydrogel that exhibits temperature-sensitive phase transitions;

Introducing a liquid sample containing proteins to the substrate, wherein the polymer brush or hydrogel is maintained at a temperature below its lower critical solution temperature (LCST), resulting in a hydrophilic state that allows proteins to be weakly bound or suspended within the hydrogel matrix;

Increasing the temperature of the polymer brush or hydrogel to above its LCST, causing the polymer to undergo a phase transition to a hydrophobic state, thereby trapping the proteins in place through hydrophobic interactions or physical encapsulation within the collapsed polymer matrix;

Subjecting the trapped proteins to multi-frequency ultraviolet (UV) light for interrogation, wherein the UV-transparent properties of the polymer brush or hydrogel allow the transmission of UV light in the range of 250 nm-350 nm for detecting the autofluorescence of aromatic amino acids in the proteins; and Optionally decreasing the temperature below the LCST to release the trapped proteins from the polymer brush or hydrogel, allowing for a reversible trapping and release of proteins; and Single-Laser UV Detection of β-Sheet Aggregates (to detect protein aggregates associated with neurodegenerative diseases);

Exciting a biological sample with a single ultraviolet (UV) laser at a wavelength in a range of from approximately 280 nm to about 295 nm, wherein the excitation induces (i) a UV/autofluorescence emission primarily from aromatic amino acids in the range of approximately 320 nm to 370 nm, and (ii) an additional blue emission from stacked β-sheet aggregates in the range of approximately 400 nm to 450 nm;

Collecting emission intensities in at least two detection bands (one corresponding to the UV/autofluorescence band and another corresponding to the blue emission band);

Computing a ratio of the intensity in the blue emission band relative to the intensity in the UV/autofluorescence band; and Identifying and/or quantifying the presence of stacked β-sheet protein aggregates based on the ratio, wherein an elevated blue-to-UV ratio indicates aggregated protein structures characteristic of one or more neurodegenerative conditions.

As mentioned, detection of one or more proteins as biomarkers in a biological fluid is of value in several contexts and for several purposes. These include monitoring or detection of:

The deterioration of food products, and possible health risks associated with the storage or preparation of food;

Indicators of a current state or change over time in a disease or other indicator of the health of a person;

Monitoring the state or condition of a specific chemical or biological reaction;

Monitoring or detecting sewage or pollutants in a source of water;

Monitoring or detecting leakage from an industrial process;

Environmental monitoring, including detection of pathogens, allergens, or biohazards in air, soil, or water samples;

Detection of doping agents, performance-enhancing substances, or metabolic indicators in sports and fitness settings;

Assessment of animal health, including in livestock, veterinary, or wildlife contexts;

Surveillance or early warning systems for infectious disease outbreaks in human or animal populations;

Surveillance of biological weapons, the disclosed approach is robust to genetic obfuscation techniques: Unlike DNA-based detection methods that can be evaded through codon recoding or synthetic gene design, our system operates at the protein level, directly detecting the expressed proteins. This makes it highly effective for biological warfare monitoring, as it identifies functional proteins regardless of how the underlying genetic code has been altered to bypass conventional nucleic acid-based surveillance;

Quality control in pharmaceutical or biotechnology manufacturing, including contamination detection or bioprocess monitoring;

Personalized wellness tracking, including stress, fatigue, or immune response monitoring in healthy individuals.

As one example related to health, an embodiment may be used for detecting and identifying proteins and other biomolecules that are part of a compound and that would benefit from regular monitoring:

For example, neurotransmitters and hormones derived from Aromatic amino acids:
Serotonin derived from tryptophan;
Dopamine derived from tyrosine;
Melanin derived from tyrosine;
Thyroxine is a thyroid hormone derived from tyrosine;
Epinephrine and norepinephrine are derived from tyrosine;

Some drugs and drug Metabolites also exhibit UV-emission, and their concentrations could be monitored:
The antibiotics groups Tetracycline and Fluoroquinolone;
Some Anti-malarial drugs, such as chloroquine and quinine;
Some antidepressant drugs, such as amitriptyline and imipramine;
Some Opioids such as Morphine and Codeine;
Metabolites of drugs my exhibit UV fluorescence properties. Monitoring the UV characteristics of drug metabolites can provide insights into drug metabolism and elimination pathways;

Nutritional compounds:
Niacin (Vitamin B3);

Riboflavin (Vitamin B2) (with absorption lines at 445, 370 E 520-560 nm);

Phenolic compounds such as flavonoids, coumarins, and stilbenes;

Protein aggregates can exhibit UV emission in the absence of aromatic amino acids; these can have diagnostic value for (as non-limiting examples):

Alzheimer disease;

Parkinson disease;

Huntington disease.

As mentioned, a similar diagnostic system could be used to identify and quantify other types of markers that exhibit UV emissions, including those found in non-biological fluids. As non-limiting examples, the disclosed device, system, and techniques can be used for purposes of single or continuous environmental monitoring of:

Water quality and pollutants to measure water safety;

Sewage water for drug contaminants;

Sewage water for bacteria;

Antimicrobial resistance;

Sewage water for monitoring the spread of a disease;

Chemical or industrial manufacturing processes;

Leak Detection—detection of leaks of specific chemicals in industrial settings. Some industrial solvents and agents have distinct UV fluorescence characteristics, making them detectable in complex environments where they might otherwise be invisible;

Oil Spill Identification and Analysis;

UV fluorescence can distinguish between different types of crude oil and other organic compounds— this can be crucial information for environmental monitoring and cleanup operations.

With regards to sample preparation and the measurement process, embodiments may modify the substrate to slow down Brownian motion, by "tuning" the Stokes-Einstein equation through increasing the viscosity of the fluid or lowering the temperature. Another option is to use freezing-thawing cycles. This is done to provide additional time to measure the same particles with different excitation parameters. To increase viscosity, one could (for example) mix saliva with glycerol or a viscous chemical.

Another possible use is that of analyzing interactions between different molecules with each other, given that analytes auto fluorescence under UV light. In this situation, the sample molecules can be proteins, DNA, labeled molecules, or biomolecules that fluorescence under UV exposure.

As mentioned, monitoring of personal health conditions or status is a valuable application or use of the disclosed and/or described techniques. Monitoring specific protein levels in blood or serum is a key to diagnosing, managing, and predicting outcomes for various chronic diseases. The following is a list of chronic conditions and the associated proteins that are commonly used as biomarkers for that condition or disease, and hence may be of interest to measure or monitor using an embodiment:

Stress/Burnout

Alpha-Amylase: An enzyme (and thus a protein) secreted primarily by the salivary glands. Elevated salivary alpha-amylase levels correlate with activation of the sympathetic nervous system in response to stress. Chronic elevations may indicate prolonged stress and potential burnout;

Chromogranin A (CgA): A protein found in adrenal medullary and other neuroendocrine cells. Increased levels can reflect heightened sympathetic-adrenal-medullary activity, often observed under prolonged psychological or physiological stress;

Secretory Immunoglobulin A (sIgA): A key immune protein in saliva and other mucosal surfaces. Chronic stress can reduce sIgA levels, indicating compromised mucosal immunity and increased susceptibility to stress-related health issues;

Cardiovascular Diseases

C-reactive protein (CRP): Marker of systemic inflammation; elevated levels are associated with atherosclerosis and heart disease;

Troponin: Indicator of myocardial injury; used in monitoring chronic heart failure and acute coronary syndromes;

B-type natriuretic peptide (BNP) and N-terminal proBNP (NT-proBNP): Elevated in heart failure, reflecting ventricular strain;

Lipoprotein-associated phospholipase A2 (Lp-PLA2): Predicts cardiovascular events and stroke risk.

Diabetes and Metabolic Disorders

Glycated Hemoglobin (HbAlc): Reflects long-term blood sugar control;

Insulin: Used to evaluate insulin resistance and beta-cell function;

Adiponectin and Leptin: Associated with metabolic syndrome and obesity-related inflammation;

C-peptide: Reflects endogenous insulin production.

Chronic Kidney Disease (CKD)

Cystatin C: Sensitive marker for glomerular filtration rate (GFR);

Albumin: Low levels indicate kidney damage or proteinuria;

Beta-2 microglobulin: Elevated in kidney dysfunction.

Chronic Liver Disease

Alpha-fetoprotein (AFP): Monitored in chronic liver disease for hepatocellular carcinoma risk;

Albumin: Low levels suggest impaired liver synthetic function;

Alanine aminotransferase (ALT) and Aspartate aminotransferase (AST): Reflect liver inflammation and damage.

Autoimmune and Inflammatory Diseases

Antinuclear Antibodies (ANA): Present in systemic lupus erythematosus (SLE) and other autoimmune diseases;

Rheumatoid Factor (RF) and Anti-cyclic Citrullinated Peptide (Anti-CCP): Associated with rheumatoid arthritis;

Calprotectin: Marker for inflammatory bowel disease (IBD).

Cancer

Prostate-Specific Antigen (PSA): Monitored in prostate cancer;

CA-125: Associated with ovarian cancer;

HER2/neu: Biomarker for breast cancer progression and response to therapy;

Carcinoembryonic Antigen (CEA): Monitored in colorectal and other cancers.

Neurodegenerative Diseases

Amyloid Beta and Tau Proteins: Associated with Alzheimer's disease; emerging blood tests aim to detect early changes;

Neurofilament Light Chain (NfL): Biomarker for neuronal damage in multiple sclerosis and other neurodegenerative diseases.

Chronic Respiratory Diseases

Surfactant Proteins (SP-A, SP-D): Indicative of lung injury or fibrosis in chronic obstructive pulmonary disease (COPD) and interstitial lung diseases;

IgE: Elevated in chronic asthma and allergic diseases.

Chronic Infectious Diseases

Hepatitis B and C Viral Proteins (e.g., HBsAg, HCV Core Antigen): Monitored in chronic hepatitis infections;

HIV Proteins (e.g., p24 antigen): Used alongside viral load to monitor HIV progression and treatment response.

Bone and Joint Disorders.

Osteocalcin and Bone-Specific Alkaline Phosphatase (BSAP): Monitored in osteoporosis;

Collagen Breakdown Products (e.g., CTX, NTX): Reflect bone resorption in metabolic bone diseases.

As the above examples suggest, there are multiple advantages to monitoring protein biomarkers in the context of personal health. These include:

Early Diagnosis: Proteins often change in the early stages of disease, allowing for earlier intervention;

Disease Progression Monitoring: Regular measurement provides insights into how a disease is progressing or responding to treatment;

Personalized Medicine: Biomarker levels can guide therapy decisions, such as selecting treatments tailored to individual needs.

Embodiments may be used to determine the proteins or components of a biofluid, a tissue sample or a cell. In some example uses, a light-emitting compound can be added to a sample to create a signature of an amino acid that might not naturally respond to the incident UV excitation. This can be used to assist in differentiating between proteins having a similar spectrum. The detector may be an array of CMOS pixels, a photodiode (such as a UV optical diode used in conjunction with an appropriate filter), or a CCD array, as non-limiting examples. The optical elements may be one or more dichroic mirrors, waveguides, holographic elements, or lenses, as non-limiting examples. The optical elements may be used to "map" each nanophotonic structure to a pixel of a detector.

As mentioned, the conditions under which a spectra or spectrum is collected from a sample as part of identifying the proteins in the sample, and/or as part of constructing a reference database may be varied to produce more easily distinguishable spectra or spectrum. These conditions may include inducing temperature variations during measurements, the cleaving of molecules in a sample to more readily isolate proteins, the denaturing of a sample (e.g., using Urea or guanidineHCL), implementing a Red Edge Excitation Shift (REES) technique, where instead of exciting a molecule at the peak absorption wavelength, instead exciting at progressively longer wavelengths (closer to the red edge of the absorption spectrum), an emission shift observation (where if a fluorophore compound is in a highly restricted environment (e.g., buried in a protein or in a viscous solvent), the emitted fluorescence shifts toward longer wavelengths as the excitation wavelength increases, altering the viscosity of a sample, applying a fractionalization technique such as one based on size, affinity, or isoelectric focusing.

In one embodiment, the output of the disclosed device is an indication of one or more of a protein responsible for the collected spectra or spectrum, a disease or condition that may be suggested by the presence of one or more identified proteins, or a change in a disease or condition over time as indicated by a change in the amount or type of protein found in a sample. In some embodiments, characteristics of the UV emission by a sample may be noted, such as strength of emission, lifetime of emission, or change in UV emissions over time.

The disclosure includes the following clauses and embodiments:

1. An apparatus for identifying protein composition of a biofluid, comprising:

a substrate on which to place a sample of a biofluid, the substrate including one or more nanophotonic structures which enhance UV fluorescence by a protein in the sample when the sample is irradiated;

a source of UV radiation positioned to illuminate the sample, and operable to generate radiation at a plurality of wavelengths ranging from 180 nm to 350 nm and a plurality of power levels;

one or more optical elements to focus the UV radiation from the source onto the substrate;

a detector to receive photons from the substrate and in response to generate a signal or signals representing one or more wavelengths of the received photons; and a process or processes executed by a programmed processor to identify a protein in the sample based on the generated signal or signals, wherein the process or processes include using a trained model that takes as an input a spectrum of photons and in response outputs a protein predicted to be responsible for the spectrum.

2. The apparatus of clause 1, wherein the protein includes one or more of the amino acids Tryptophan, Tyrosine, or Phenylalanine, and the sample is a biofluid.

3. The apparatus of clause 2, wherein the source of UV radiation is a combination of several laser or LEDs, and is pulsed, or continuous wave, and further wherein the source is capable of producing UV light in an adjustable wavelength range substantially between 180 nm and 350 nm.

4. The apparatus of clause 1, wherein the optical elements include one or more of lenses, dichroic mirrors, and holographic elements, and operate to map or direct photons from the nanophotonic structure or structures onto the detector.

5. The apparatus of clause 1, wherein the detector is a CMOS device configured to operate as a spectrometer.

6. The apparatus of clause 1, wherein the substrate includes one or more micro-fluidic elements that assist in separating the sample of the biofluid into different components.

7. The apparatus of clause 1, wherein the nanophotonic structures are one or more of a nano-aperture, UV dimer antenna, or zero mode waveguide.

8. The apparatus of clause 1, wherein the process or processes executed by the programmed processor generate an indication of a disease or condition that is indicated by the detected protein or proteins in the sample of the biofluid.

9. A method for detecting a protein in a biofluid, comprising:

obtaining a database of measurements of UV fluorescence for each of multiple proteins, where the proteins are in pure form, in a biofluid, or in an artificial mixture, and where the measurements are conducted at multiple wavelengths and powers of incident UV radiation;

placing a sample of a biofluid on a substrate, where the substrate operates to enhance a signal generated by a protein in response to UV irradiation;

irradiating the sample by a UV source at one or more wavelengths and one or more powers;

directing the generated photons from the substrate using one or more optical elements;

detecting the directed photons by a spectrometer;

processing the output by the spectrometer using a trained model;

identifying a protein responsible for the signal or signals generated by the spectrometer in response to detecting the directed photons; and outputting an indicator of the identified protein in the sample of the biofluid and its corresponding quantity.

10. The method of clause 9, wherein the substrate comprises one or more nanophotonic structures which serve to enhance or amplify the signal or signals generated by the protein as well as create a sub-diffraction volume, where each sub-diffraction volume acts as a detection site for a different protein composition and provides a unique data point as part of predicting an overall composition of a biofluid.

11. The method of clause 9, wherein the trained model performs spectral unmixing or decomposition, followed by data processing to prepare the output of the spectrometer for identification as being produced by a specific protein.

12. The method of clause 9, wherein the database of UV fluorescence from single molecule of pure proteins is used to create training data for the trained model, and further, wherein the trained model operates to generate an identifier of a protein responsible for a spectrum input to the model.

13. The method of clause 9, further comprising adding amino acid-targeting dyes or Flurophobes to the sample of the biofluid, the dyes or Flurophobes binding to non-light emitting amino acids to provide an optical signature.

14. The method of clause 9 where the detector is a combination of an interference filter and UV optical diode.

15. The method of clause 9 wherein a device implementing one or more steps of the method is fabricated on a semiconductor chip, the chip including a CMOS image sensor, one or more waveguides to input UV light, drivers to control UV light inputs, nanophotonic structures and optical elements to direct light to the detector.

16. The method of clause 9, wherein outputting an indicator of the identified protein in the sample of the biofluid and its corresponding quantity further comprises outputting one or more of a strength of UV emission, a lifetime of UV emission, and evolution of UV emission strength as a function of power of illumination and a diffusion time of proteins inside a nanophotonic structure.

17. The method of clause 12, further comprising updating UV emission properties and signatures of proteins and biomolecules from biofluid samples.

18. The method of clause 9, wherein a ratio of aromatic amino acids or other UV emitting elements in a protein or biomolecule is used to identify a protein or biomolecule that is part of a heterogenous mixture.

19. The method of clause 9, wherein a signal or signals from the sample of the biofluid is compared to one or more states of a biological sample that has previously been characterized.

20. The method of clause 9, further comprising using a fractionation method to presort proteins before illuminating the sample, the fraction method including one or more of size, affinity, or isoelectric focusing.

Embodiments as disclosed and/or described herein can be implemented in the form of control logic using computer software in a modular or integrated manner. Based on the disclosure and teachings provided herein, a person of ordinary skill in the art will know and appreciate other ways and/or methods to implement the present invention using hardware and a combination of hardware and software.

In some embodiments, certain of the methods, models or functions disclosed and/or described herein may be embodied in the form of a trained neural network, where the network is implemented by the execution of a set of computer-executable instructions or representation of a data structure. The instructions may be stored in (or on) a non-transitory computer-readable medium and executed by a programmed processor or processing element. The set of instructions may be conveyed to a user through a transfer of instructions or an application that executes a set of instructions (such as over a network, e.g., the Internet). The set of instructions or an application may be utilized by an end-user through access to a SaaS platform or a service provided through such a platform. A trained neural network, trained machine learning model, or other form of decision or classification process may be used to implement one or more of the methods, functions, processes, or operations disclosed and/or described herein. Note that a neural network or deep learning model may be characterized in the form of a data structure in which are stored data representing a set of layers containing nodes, and connections between nodes in different layers are created (or formed) that operate on an input to provide a decision or value as an output.

In general terms, a neural network may be viewed as a system of interconnected artificial "neurons" that exchange messages between each other. The connections have numeric weights that are "tuned" during a training process, so that a properly trained network will respond correctly when presented with an image or pattern to recognize (for example). In this characterization, the network consists of multiple layers of feature-detecting "neurons"; each layer has neurons that respond to different combinations of inputs from the previous layers. Training of a network is performed using a "labeled" dataset of inputs in a wide assortment of representative input patterns that are associated with their intended output response. Training uses general-purpose methods to iteratively determine the weights for intermediate and final feature neurons. In terms of a computational model, each neuron calculates the dot product of inputs and weights, adds the bias, and applies a non-linear trigger or activation function (for example, using a sigmoid response function).

Machine learning (ML) is being used more and more to enable the analysis of data and assist in making decisions in multiple industries. To benefit from using machine learning, a machine learning algorithm is applied to a set of training data and labels to generate a "model" which represents what the application of the algorithm has "learned" from the training data. Each element (or example, in the form of one or more parameters, variables, characteristics or "features") of the set of training data is associated with a label or annotation that defines how the element should be classified by the trained model. A machine learning model is a set of layers of connected neurons that operate to make a decision (such as a classification) regarding a sample of input data. When trained (i.e., the weights connecting neurons have converged and become stable or within an acceptable amount of variation), the model will operate on a new element of input data to generate the correct label or classification as an output.

Any of the software components, processes or functions described in this application may be implemented as software code to be executed by a processor using any suitable computer language such as Python, Java, JavaScript, C++ or Perl using conventional or object-oriented techniques. The software code may be stored as a series of instructions, or commands in (or on) a non-transitory computer-readable medium, such as a random-access memory (RAM), a read only memory (ROM), a magnetic medium such as a hard-drive or a floppy disk, or an optical medium such as a CD-ROM. In this context, a non-transitory computer-readable medium is almost any medium suitable for the storage of data or an instruction set aside from a transitory waveform. Any such computer readable medium may reside on or within a single computational apparatus and may be present on or within different computational apparatuses within a system or network.

According to one example implementation, the term processing element or processor, as used herein, may be a central processing unit (CPU), or conceptualized as a CPU (such as a virtual machine). In this example implementation, the CPU or a device in which the CPU is incorporated may be coupled, connected, and/or in communication with one or more peripheral devices, such as display. In another example implementation, the processing element or processor may be incorporated into a mobile computing device, such as a smartphone or tablet computer.

The non-transitory computer-readable storage medium referred to herein may include a number of physical drive units, such as a redundant array of independent disks (RAID), a floppy disk drive, a flash memory, a USB flash drive, an external hard disk drive, thumb drive, pen drive, key drive, a High-Density Digital Versatile Disc (HD-DVD) optical disc drive, an internal hard disk drive, a Blu-Ray optical disc drive, or a Holographic Digital Data Storage (HDDS) optical disc drive, synchronous dynamic random access memory (SDRAM), or similar devices or other forms of memories based on similar technologies. Such computer-readable storage media allow the processing element or processor to access computer-executable process steps, application programs and the like, stored on removable and non-removable memory media, to off-load data from a device or to upload data to a device. As mentioned, with regards to the embodiments described herein, a non-transitory computer-readable medium may include almost any structure, technology or method apart from a transitory waveform or similar medium.

Certain implementations of the disclosed technology are described herein with reference to block diagrams of systems, and/or to flowcharts or flow diagrams of functions, operations, processes, or methods. It will be understood that one or more blocks of the block diagrams, or one or more stages or steps of the flowcharts or flow diagrams, and combinations of blocks in the block diagrams and stages or steps of the flowcharts or flow diagrams, respectively, may be implemented by computer-executable program instructions. Note that in some embodiments, one or more of the blocks, or stages or steps may not necessarily need to be performed in the order presented or may not necessarily need to be performed at all.

The computer-executable program instructions may be loaded onto a general-purpose computer, a special purpose computer, a processor, or other programmable data processing apparatus to produce a specific example of a machine, such that the instructions that are executed by the computer, processor, or other programmable data processing apparatus create means for implementing one or more of the functions, operations, processes, or methods described herein. These computer program instructions may also be stored in a computer-readable memory that may direct a computer or other programmable data processing apparatus to function in a specific manner, such that the instructions stored in the computer-readable memory produce an article of manufacture including instruction means that implement one or more of the functions, operations, processes, or methods described herein.

While certain implementations of the disclosed technology have been described in connection with what is presently considered to be the most practical and various implementations, it is to be understood that the disclosed technology is not to be limited to the disclosed implementations. Instead, the disclosed implementations are intended to cover various modifications and equivalent arrangements included within the scope of the appended claims. Although specific terms are employed herein, they are used in a generic and descriptive sense only and not for purposes of limitation.

This written description uses examples to disclose certain implementations of the disclosed technology, and also to enable any person skilled in the art to practice certain implementations of the disclosed technology, including making and using any devices or systems and performing any incorporated methods. The patentable scope of certain implementations of the disclosed technology is defined in the claims, and may include other examples that occur to those skilled in the art. Such other examples are intended to be within the scope of the claims if they have structural and/or functional elements that do not differ from the literal language of the claims, or if they include structural and/or functional elements with insubstantial differences from the literal language of the claims.

All references, including publications, patent applications, and patents cited herein are hereby incorporated by reference to the same extent as if each reference were individually and specifically indicated to be incorporated by reference and/or were set forth in its entirety herein.

The use of the terms "a" and "an" and "the" and similar referents in the specification and in the following claims are to be construed to cover both the singular and the plural, unless otherwise indicated herein or clearly contradicted by context. The terms "having," "including," "containing" and similar referents in the specification and in the following claims are to be construed as open-ended terms (e.g., meaning "including, but not limited to,") unless otherwise noted.

Recitation of ranges of values herein are merely intended to serve as a shorthand method of referring individually to each separate value inclusively falling within the range, unless otherwise indicated herein, and each separate value is incorporated into the specification as if it were individually recited herein.

All methods described herein may be performed in any suitable order unless otherwise indicated herein or clearly contradicted by context. The use of any and all examples, or exemplary language (e.g., "such as") provided herein, is intended merely to better illuminate embodiments of the disclosure and does not pose a limitation to the scope of the invention unless otherwise claimed. No language in the specification should be construed as indicating any non-claimed element as essential to each embodiment of the present invention.

As used herein (i.e., the claims, figures, and specification), the term "or" is used inclusively to refer items in the alternative and in combination.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

Which is claimed is:

1. An apparatus for identifying protein composition of a biofluid, comprising:

a substrate on which to place a sample of a biofluid, the substrate including one or more nanophotonic structures which enhance UV fluorescence by a protein in the sample when the sample is irradiated and create a sub-diffraction volume, where each sub-diffraction volume acts as a detection site for a different position;

a source of UV radiation positioned to illuminate the sample, and operable to generate radiation at a plurality of wavelengths ranging from 180 nm to 350 nm and a plurality of power levels;

one or more optical elements to focus the UV radiation from the source onto the substrate;

a detector to receive photons from the substrate and in response to generate a signal or signals representing one or more wavelengths of the received photons; and a process or processes executed by a programmed processor to identify a protein in the sample based on the generated signal or signals, wherein the process or processes include using a trained model that takes as an input a spectrum of photons and in response outputs a protein predicted to be responsible for the spectrum, wherein the model is trained using training da constructed from a database of measurements of UV fluorescence for each of multiple proteins, where the multiple proteins are in pure form, in a biofluid, or in an artificial mixture, and where the measurements are conducted at multiple wavelengths and powers of incident UV radiation.

2. The apparatus of claim 1, wherein the protein includes one or more of the amino acids Tryptophan, Tyrosine, or Phenylalanine, and the sample is a biofluid.

3. The apparatus of claim 2, wherein the source of UV radiation is a combination of several laser or LEDs, and is pulsed, or continuous wave, and further wherein the source is capable of producing UV light in an adjustable wavelength range substantially between 180 nm and 350 nm.

4. The apparatus of claim 1, wherein the optical elements include one or more of lenses, dichroic mirrors, and holographic elements, and operate to map or direct photons from the nanophotonic structure or structures onto the detector.

5. The apparatus of claim 1, wherein the detector is a CMOS device configured to operate as a spectrometer.

6. The apparatus of claim 1, wherein the substrate includes one or more micro-fluidic elements that assist in separating the sample of the biofluid into different components.

7. The apparatus of claim 1, wherein the nanophotonic structures are one or more of a nano-aperture, UV dimer antenna, or zero mode waveguide.

8. The apparatus of claim 1, wherein the process or processes executed by the programmed processor generate an indication of a disease or condition that is indicated by the detected protein or proteins in the sample of the biofluid.

9. The apparatus of claim 1, wherein the nanophotonic-microfluidic substrate comprises nanostructures fabricated on a silica base, optionally coated with aluminum or rhodium to increase quantum yield, and includes micro-nano-channels configured to segregate analytes by molecular weight.

10. The apparatus of claim 1, wherein the detection unit is configured to capture UV emission spectra in the range of 250 nm to 500 nm, and comprises a CMOS spectrometer, CCD, or an optical bandpass filter system, and may operate in single or multi-sensor arrangements to enable parallel sample processing.

11. A method for detecting a protein in a biofluid, comprising:

obtaining a database of measurements of UV fluorescence for each of multiple proteins, where the proteins are in pure form, in a biofluid, or in an artificial mixture, and where the measurements are conducted at multiple wavelengths and powers of incident UV radiation;

placing a sample of a biofluid on a substrate, where the substrate operates to enhance a signal generated by a protein in response to UV irradiation;

irradiating the sample by a UV source at one or more wavelengths and one or more powers;

directing the generated photons from the substrate using one or more optical elements;

detecting the directed photons by a spectrometer;

processing the output by the spectrometer using a trained model;

identifying a protein responsible for the signal or signals generated by the spectrometer in response to detecting the directed photons; and outputting an indicator of the identified protein in the sample of the biofluid and its corresponding quantity.

12. The method of claim 11, wherein the substrate comprises one or more nanophotonic structures which serve to enhance or amplify the signal or signals generated by the protein as well as create a sub-diffraction volume, where each sub-diffraction volume acts as a detection site for a different protein composition and provides a unique data point as part of predicting an overall composition of a biofluid.

13. The method of claim 11, wherein the trained model performs spectral unmixing or decomposition, followed by data processing to prepare the output of the spectrometer for identification as being produced by a specific protein.

14. The method of claim 11, wherein the database of UV fluorescence from single molecule of pure proteins is used to create training data for the trained model, and further, wherein the trained model operates to generate an identifier of a protein responsible for a spectrum input to the model.

15. The method of claim 14, further comprising updating UV emission properties and signatures of proteins and biomolecules from biofluid samples.

16. The method of claim 11, further comprising adding amino acid-targeting dyes or Flurophorses to the sample of the biofluid, the dyes or Flurophorbes binding to non-light emitting amino acids to provide an optical signature.

17. The method of claim 11 where the detector is a combination of an interference filter and UV optical diode.

18. The method of claim 11 wherein a device implementing one or more steps of the method is fabricated on a semiconductor chip, the chip including a CMOS image sensor, one or more waveguides to input UV light, drivers to control UV light inputs, nanophotonic structures and optical elements to direct light to the detector.

19. The method of claim 11, wherein outputting an indicator of the identified protein in the sample of the biofluid and its corresponding quantity further comprises outputting one or more of a strength of UV emission, a lifetime of UV emission, and evolution of UV emission strength as a function of power of illumination and a diffusion time of proteins inside a nanophotonic structure.

20. The method of claim 11, wherein a ratio of aromatic amino acids or other UV emitting elements in a protein or biomolecule is used to identify a protein or biomolecule that is part of a heterogenous mixture.

21. The method of claim 11, wherein a signal or signals from the sample of the biofluid is compared to one or more states of a biological sample that has previously been characterized.

22. The method of claim 11, further comprising using a fractionation method to presort proteins before illuminating the sample, the fraction method including one or more of size, affinity, or isoelectric focusing.

23. The method of claim 11, wherein the sample comprises non-biofluid materials including tissue homogenates, single-cell lysates, or synthetic mixtures containing UV-emitting biomolecules.

24. The method of claim 11, further comprising adding fluorogenic dyes or amino acid-specific fluorophores to bind non-UV-emitting amino acids, thereby providing them with an optical signature detectable under UV excitation.

25. The method of claim 11, wherein the spectrometer includes a configuration of interference filters and UV optical diodes tuned to differentiate spectral signals from distinct analytes within a mixed sample.

26. The method of claim 11, wherein the device is implemented as an integrated photonic chip built on CMOS architecture, comprising a nanophotonic substrate, waveguides for UV input, drivers for controlling UV excitation, and holographic elements for dispersing signals to a CMOS detector.

27. The method of claim 11, further comprising measuring fluorescence decay lifetime information as part of the signal, where such lifetime signatures contribute to biomolecule identification.

28. The method of claim 11, wherein signal strength, emission lifetime, or evolution of fluorescence over time are recorded to aid in identification of biomolecules.

29. A method for identifying proteins using UV-induced autofluorescence and thermal denaturation profiling, comprising:

irradiating the sample under controlled temperature ramping;

detecting temperature-dependent changes in the sample's UV autofluorescence; and identifying proteins in the sample based on their thermal unfolding signatures.

30. A system for enhanced protein detection via combined UV autofluorescence and amino acid-specific turn-on dyes, comprising:

a dye delivery module;

a dual-channel detection system for UV and visible fluorescence; and a processor for integrating spectral information from both UV and visible sources to enhance detection of a specific protein.

* * * * *